US011260223B2

(12) United States Patent
Samejima et al.

(10) Patent No.: US 11,260,223 B2
(45) Date of Patent: Mar. 1, 2022

(54) LOW-FREQUENCY TREATMENT DEVICE AND TREATMENT SYSTEM

(71) Applicant: OMRON HEALTHCARE Co., Ltd., Kyoto (JP)

(72) Inventors: Mitsuru Samejima, Kyoto (JP); Yui Watanabe, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 39 days.

(21) Appl. No.: 16/775,549

(22) Filed: Jan. 29, 2020

(65) Prior Publication Data

US 2020/0238079 A1 Jul. 30, 2020

Related U.S. Application Data

(63) Continuation of application No. PCT/JP2018/026459, filed on Jul. 13, 2018.

(30) Foreign Application Priority Data

Aug. 30, 2017 (JP) .............................. JP2017-165056

(51) Int. Cl.
  *A61N 1/08* (2006.01)
  *A61N 1/40* (2006.01)
  *A61N 1/02* (2006.01)
  *A61N 1/04* (2006.01)

(52) U.S. Cl.
  CPC .............. *A61N 1/08* (2013.01); *A61N 1/403* (2013.01); *A61N 1/025* (2013.01); *A61N 1/0492* (2013.01)

(58) Field of Classification Search
  CPC .......... A61N 1/08; A61N 1/025; A61N 1/403; A61N 1/0492
  See application file for complete search history.

(56) References Cited

U.S. PATENT DOCUMENTS

2016/0228640 A1 8/2016 Pindado et al.
2017/0259072 A1* 9/2017 Newham ............ A61N 1/37254
2018/0345014 A1* 12/2018 Gozani ................ A61N 1/3603

FOREIGN PATENT DOCUMENTS

JP 2004173800 A 6/2004
JP 2005-065745 A 3/2005

(Continued)

OTHER PUBLICATIONS

Strusberg I, Mendelberg RC, Serra HA, Strusberg AM. Influence of weather conditions on rheumatic pain. J Rheumatol. Feb. 2002; 29(2):335-8. PMID: 11838853. (Year: 2002).*

(Continued)

Primary Examiner — Michael W Kahelin
Assistant Examiner — Michael A Rizzuto
(74) Attorney, Agent, or Firm — Birch, Stewart, Kolasch & Birch, LLP

(57) ABSTRACT

A low-frequency treatment device and a treatment system with enhanced user convenience. An acquisition unit acquires an atmospheric pressure of a position where the low-frequency treatment device is located (step S102), a determination unit determines whether the atmospheric pressure is less than a threshold (step S104), and a treatment portion increases an intensity of low frequency treatment if the atmospheric pressure is less than the threshold (step S108).

10 Claims, 17 Drawing Sheets

(56) References Cited

FOREIGN PATENT DOCUMENTS

| JP | 2005-152412 A | 6/2005 |
|---|---|---|
| JP | 2018038814 A | 3/2018 |

OTHER PUBLICATIONS

International Search Report of the International Searching Authority for PCT/JP2018/026459 dated Oct. 23, 2018.
Translation of the International Search Report of the International Searching Authority for PCT/JP2018/026459 dated Oct. 23, 2018.
Japanese Decision to Grant dated May 18, 2021 for Application No. 2017-165056 with English Translation.

\* cited by examiner

| POSITION INFORMATION | TIME PERIOD | ATMOSPHERIC PRESSURE |
|---|---|---|
| LONGITUDE X1, LATITUDE Y1 | T1 TO T2 | Z1 (hPa) |
| | T2 TO T3 | Z2 (hPa) |
| | ⋮ | ⋮ |
| LONGITUDE X2, LATITUDE Y2 | T1 TO T2 | Z3 (hPa) |
| | T2 TO T3 | Z4 (hPa) |
| | ⋮ | ⋮ |
| ⋮ | ⋮ | ⋮ |

| POSITION INFORMATION | FACILITY INFORMATION | TREATMENT CONTENT INFORMATION |
|---|---|---|
| LONGITUDE X11, LATITUDE Y11 | FACILITY CC (BB CITY, AA PREFECTURE) | LOW-FREQUENCY TREATMENT HEAT TREATMENT |
| LONGITUDE X12, LATITUDE Y12 | FACILITY DD (FF CITY, EE PREFECTURE) | LOW-FREQUENCY TREATMENT |
| ⋮ | ⋮ | ⋮ |

LOW-FREQUENCY TREATMENT DEVICE AND TREATMENT SYSTEM

CROSS-REFERENCE TO RELATED APPLICATIONS

This is a continuation of International Application PCT/JP2018/026459, with an international filing date of Jul. 13, 2018, and JP 2017-165056 with an international filing date of Aug. 30, 2017, and filed by applicant, the disclosure of which is hereby incorporated by reference in its entirety.

TECHNICAL FIELD

The present disclosure relates to a low-frequency treatment device and a treatment system.

BACKGROUND ART

Known low-frequency treatment devices are configured to apply electrical stimulation to an area of the user's body by outputting a low-frequency pulse to the area via an electrode pad. For example, Patent Document 1 describes a low-frequency treatment device with an output intensity that is able to be set by a user.

CITATION LIST

Patent Literature

Patent Document 1: JP 2005-152412 A

SUMMARY OF INVENTION

Technical Problem

The low-frequency treatment device of Patent Document 1 lacks in user convenience as the user must adjust the output intensity when the pain affecting the body of the user increases.

The present disclosure has been made in view of the circumstances described above, and a low-frequency treatment device with enhanced user convenience according to an embodiment is described. A treatment system with enhanced user convenience according to another embodiment is also described.

Solution to Problem

A low-frequency treatment device according to an embodiment of the disclosure includes:
an acquisition unit that acquires a weather parameter relating to weather, the weather parameter being a parameter that causes an increase of body pain of a user;
a treatment portion that performs low frequency treatment; and
an adjustment unit that adjusts an intensity of the low frequency treatment on the basis of the weather parameter and a predetermined threshold.

In some embodiments, the acquisition unit acquires an atmospheric pressure or an air temperature as the weather parameter for a position where the low-frequency treatment device is located; and
the adjustment unit, in a case where the atmospheric pressure or the air temperature acquired by the acquisition unit is determined to be less than a first threshold, adjusts and increases the intensity of the low frequency treatment.

In some embodiments, the adjustment unit includes a generation unit that generates a treatment current and executes processing to increase the intensity of the low frequency treatment by increasing an amplitude of a waveform of the treatment current.

In some embodiments, the treatment portion is configured to perform heat treatment; and
the adjustment unit, in a case where the atmospheric pressure or the air temperature acquired by the acquisition unit is determined to be less than the first threshold, adjusts and increases an intensity of the heat treatment.

Some embodiments further include a first notification portion that, in a case where the atmospheric pressure or the air temperature acquired by the acquisition unit is determined to be less than the first threshold, notifies saying to refrain from going outdoors in a time period when the atmospheric pressure or the air temperature is less than the first threshold.

Some embodiments further include a position information reception portion that receives input of position information, wherein the acquisition unit acquires an atmospheric pressure or an air temperature as the weather parameter for a position indicated by the position information that the position information reception portion received via input; and
a second notification portion that, in a case where the atmospheric pressure or the air temperature acquired by the acquisition unit is determined to be less than the first threshold, notifies of a possibility of body pain of a user increasing.

In some embodiments, the acquisition unit acquires an atmospheric pressure or an air temperature as the weather parameter for a position where the low-frequency treatment device is located;
a second threshold is greater than a first threshold; and
the adjustment unit, if the atmospheric pressure or the air temperature acquired by the acquisition unit is determined to be greater than the second threshold, adjusts and decreases the intensity of the low frequency treatment.

In some embodiments, the treatment portion is configured to perform heat treatment; and
the adjustment unit, in a case where the atmospheric pressure or the air temperature acquired by the acquisition unit is determined to be greater than the second threshold, adjusts and decreases an intensity of the heat treatment.

Some embodiments further include a reception portion that receives from a user a mode that is set, the mode comprising a first mode in which the intensity of the low frequency treatment is adjusted on the basis of the weather parameter and the threshold, and a second mode in which the intensity of the low frequency treatment is not adjusted.

A treatment system according to an embodiment of the disclosure includes:
a low-frequency treatment device that performs low frequency treatment;
a notification device configured to communicate with the low-frequency treatment device; and
an acquisition unit that acquires an atmospheric pressure or an air temperature for a position where the low-frequency treatment device is located; wherein
the notification device, in a case where the atmospheric pressure or the air temperature acquired by the acquisition unit is determined to be less than a threshold, notifies saying to refrain from going outdoors in a time period when the atmospheric pressure or the air temperature is less than the threshold.

Advantageous Effects of Invention

According to this disclosure, a low-frequency treatment device and a treatment system with enhanced user convenience can be provided.

DESCRIPTION OF EMBODIMENTS

Figures 1, 2:
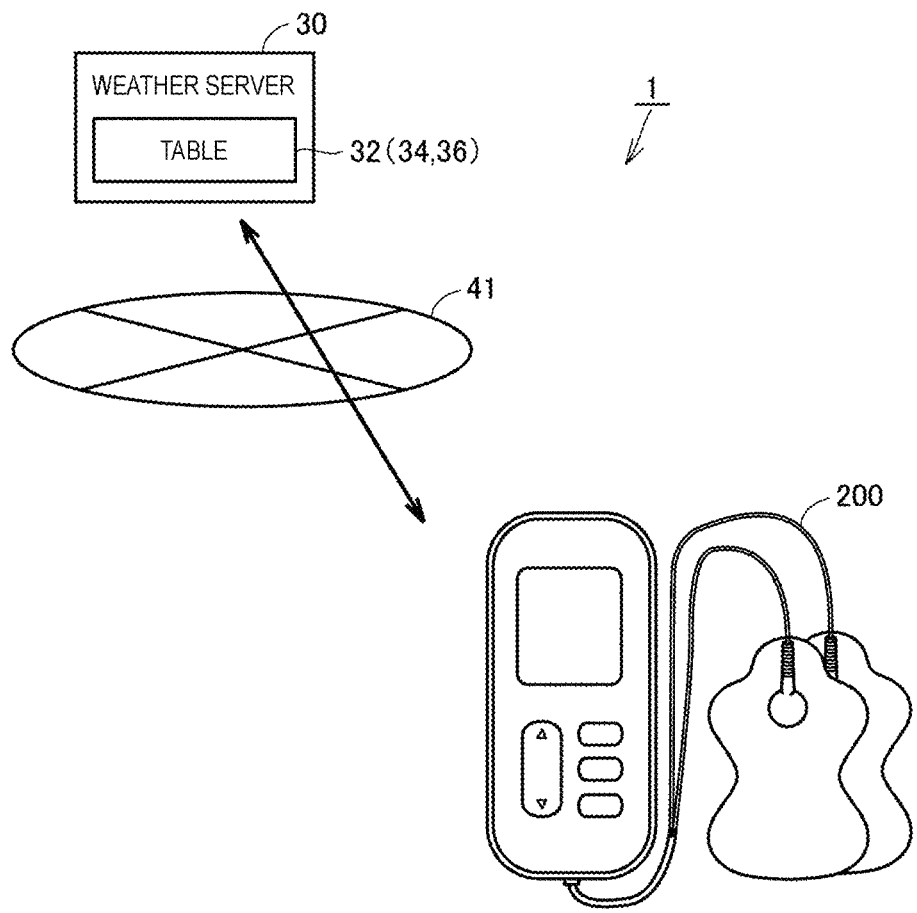
FIG. 1 is a diagram illustrating a schematic configuration of a treatment system 1.
FIG. 2 is a diagram illustrating an example of a table.

Embodiments will be described below with reference to the drawings. The same reference numerals are assigned to the same components and corresponding components, and redundant descriptions may not be repeated.

First Embodiment

System Configuration

FIG. 1 is a diagram illustrating a schematic configuration of a treatment system 1 according to a first embodiment. Referring to FIG. 1, the treatment system 1 includes a low-frequency treatment device 200, a weather server 30, and a network 41. The network 41 includes various networks such as the Internet, a mobile terminal communication network, and the like to connect the low-frequency treatment device 200 and the weather server 30 to each other.

The weather server 30 includes a table 32. The table 32 specifies information including position information and atmospheric pressure information associated together. The atmospheric pressure information indicates the atmospheric pressure of a position specified by the position information. FIG. 2 illustrates an example of the table 32. The position information in the example of FIG. 2 includes a longitude X and a latitude Y, and the unit of atmospheric pressure is hectopascal (hPa). In the example of FIG. 2, the position information includes a longitude X1 and a latitude Y1, and the associated atmospheric pressure is Z1 (hPa). This means that the atmospheric pressure at a position with the longitude X1 and the latitude Y1 is Z1 (hPa). The weather server 30 repeatedly updates the atmospheric pressure information of each position specified in the table 32 with the latest atmospheric pressure information every predetermined amount of time (for example, every hour).

Configuration of Low-Frequency Treatment Device 200

Figure 3:
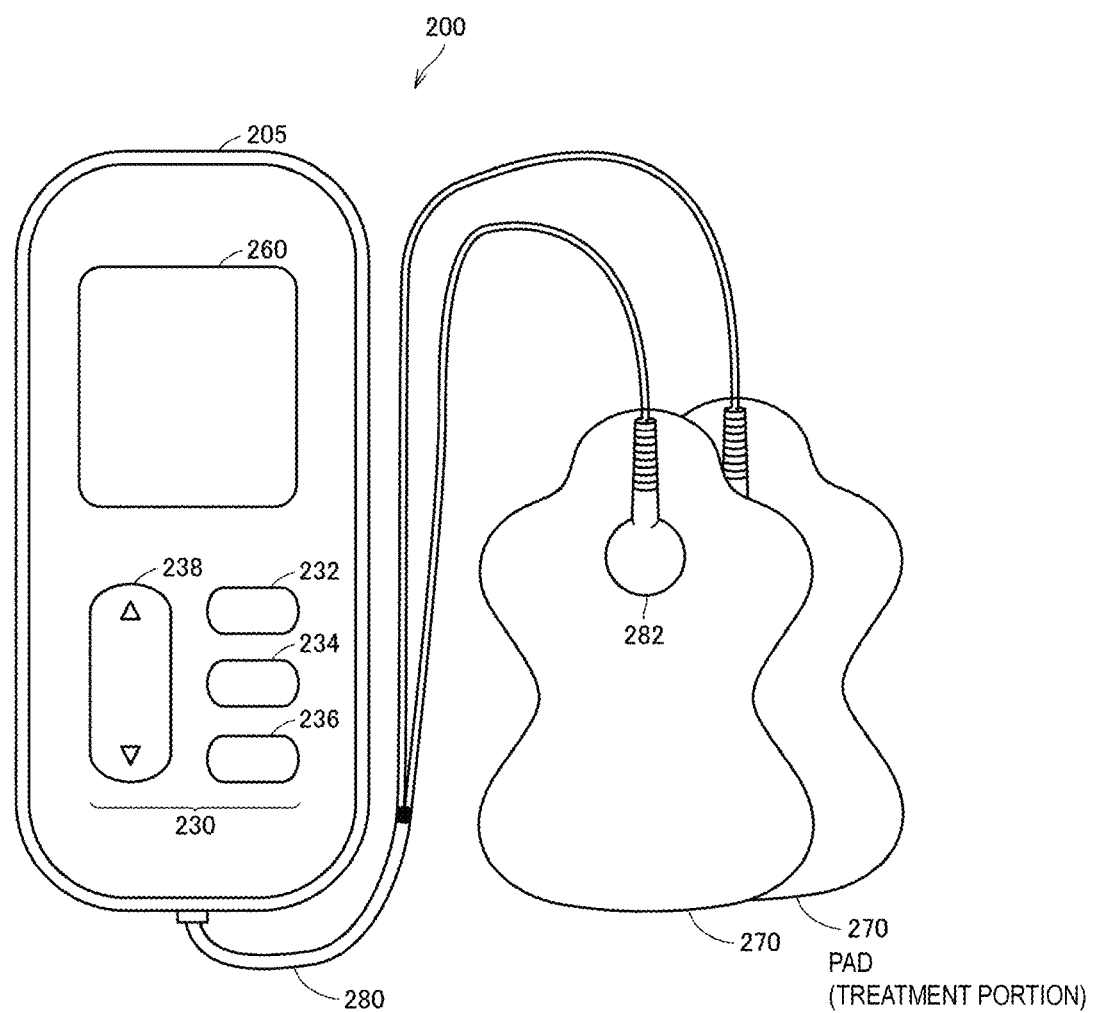
FIG. 3 is a diagram illustrating the appearance of a low-frequency treatment device 200.

FIG. 3 is a diagram illustrating an example of the appearance of the low-frequency treatment device 200 according to the first embodiment. Referring to FIG. 3, the low-frequency treatment device 200 according to the first embodiment include a main body portion 205, a pair of pads 270 attachable to a treatment site of the user, and a cord 280 for electrically connecting together the main body portion 205 and the pads 270. The pads 270 are examples of a "treatment portion" that is configured to come into contact with an area of the body. The low-frequency treatment device 200 is a wired type device that provides treatment such as easing the shoulder stiffness of the user by supplying a low-frequency pulse. For example, the frequency of the low-frequency pulse current is from 1 Hz to 1200 Hz. However, the low-frequency treatment device 200 may be configured to use a pulse current of other frequency bands.

The pads 270 each have a sheet-like shape and are configured to attach to the user's body. A first surface of the pad 270 (the surface that does not come into contact with the body) is provided with a plug that corresponds to an electrode (not illustrated) formed on a second surface (the surface that comes into contact with the body). The electrode is formed from a conductive gel-like material, for example. To connect the main body portion 205 and the pad 270, a plug 282 of the cord 280 is connected to the plug on the pad 270 and the cord 280 is inserted into the jack on the main body portion 205. Note that when the polarity of the electrode formed on one of the pads 270 is positive, the polarity of the electrode formed on the other pad 270 is negative.

The main body portion 205 includes an operation interface 230 including various buttons; and a display 260. The operation interface 230 includes a power button 232 for switching the power source on and off, a mode selection button 234 for selecting a treatment mode, a treatment start button 236, and an adjustment button 238 for adjusting the intensity of the electrical stimulation (also referred to below as "electrical stimulation intensity"). Note that the operation interface 230 is not limited to the configuration described above and may have any configuration that allows the user to perform various operations. The operation interface 230 may include other buttons, a dial, and a switch.

The electrical stimulation intensity, the remaining treatment time, the treatment mode, the attachment state of the pads 270, and the like are displayed on the display 260. Various messages are also displayed on the display 260.

Hardware Configuration

Figure 4:
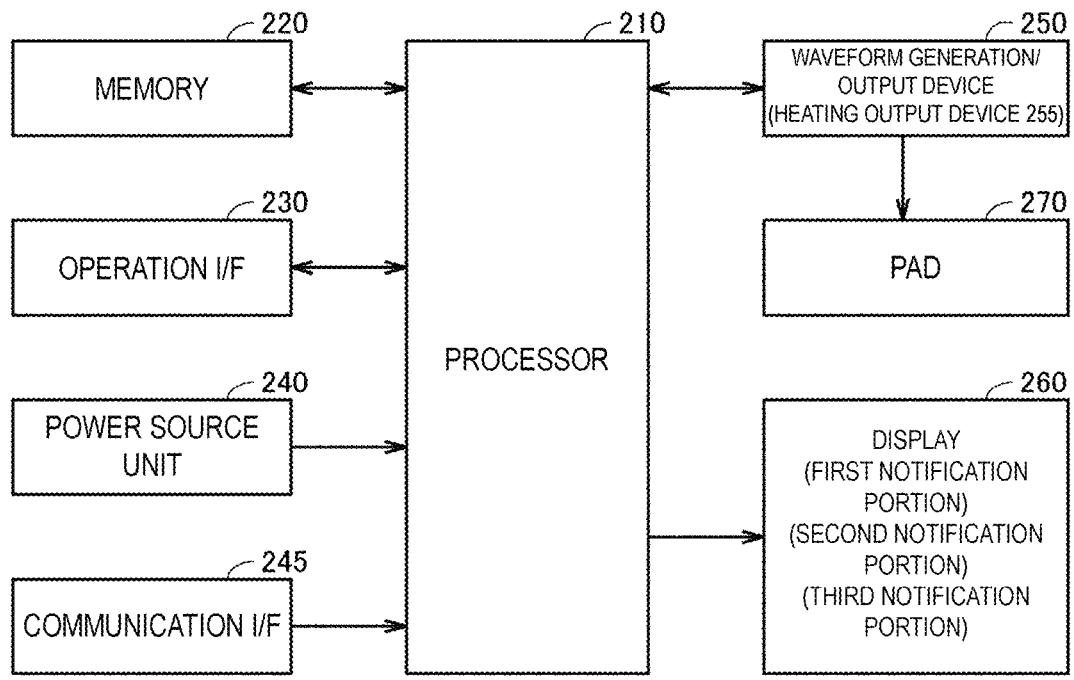
FIG. 4 is a diagram schematically illustrating the internal configuration of the low-frequency treatment device 200.

FIG. 4 is a block diagram illustrating an example of a hardware configuration of the low-frequency treatment device 200 according to the first embodiment. Referring to FIG. 4, the low-frequency treatment device 200 includes a processor 210, a memory 220, the operation interface 230, a power source unit 240, a communication interface 245, a waveform generation/output device 250, and the display 260.

The processor 210 typically may be an arithmetic processing unit such as a central processing unit (CPU) or a multi processing unit (MPU). The processor 210 functions as a control unit that controls the operation of components of the low-frequency treatment device 200 by reading out and executing a program stored in the memory 220. By executing the program, the processor 210 executes processing (steps) of the low-frequency treatment device 200 described later.

The memory 220 is realized by random access memory (RAM), read-only memory (ROM), flash memory, and/or the like. The memory 220 stores programs executed by the processor 210, data used by the processor 210, and the like.

The operation interface 230 receives an operation input to the low-frequency treatment device 200 and includes various buttons such as those described above. When the user operates the buttons, a signal corresponding to the operation is input to the processor 210.

The power source unit 240 supplies power to the constituent elements of the low-frequency treatment device 200. As the power source, an alkaline battery may be used, for example. The power source unit 240 stabilizes a battery voltage and generates a drive voltage that is supplied to the constituent elements.

The processor 210 executes the sending/receiving of various information to/from an external device such as the weather server 30 via the communication interface 245 and the network 41. The waveform generation/output device 250 outputs a current (also referred to below as a "treatment current") that flows to a treatment site on the user's body via the pads 270. The waveform generation/output device 250 includes a booster circuit, a voltage adjustment circuit, an output circuit, a current detection circuit, and the like.

The booster circuit boosts the power supply voltage to a predetermined voltage. The voltage adjustment circuit adjusts the voltage boosted by the booster circuit to a voltage corresponding to the electrical stimulation intensity set by the user. Specifically, the electrical stimulation of the low-frequency treatment device 200 can be adjusted to a predetermined number of levels (for example, ten levels) via the adjustment button 238. The processor 210 receives a setting input of the electrical stimulation intensity via the adjustment button 238 and instructs the waveform generation/output device 250 (voltage adjustment circuit) to adjust to a voltage corresponding to the received electrical stimulation intensity.

The output circuit generates a treatment waveform (pulse waveform) corresponding to the treatment mode on the basis of the voltage adjusted by the voltage adjustment circuit and outputs the treatment waveform to (the electrodes of) the pads 270 via the cord 280. Specifically, when the user performs an operation, such as switching the treatment mode or changing the electrical stimulation intensity, via the operation interface 230, a control signal corresponding to the operation content is input to the output circuit from the processor 210. The output circuit outputs a treatment waveform according to the control signal.

The low-frequency treatment device 200 is provided with a plurality of treatment modes in advance. The treatment modes include, for example, "massage", "tap", and "press".

The output circuit can generate electrical stimulations corresponding to various modes, such as "massage", "tap", "press", and the like by varying the waveform of the pulses (parameters including pulse width, pulse interval, output polarity). Also, by varying the amplitude of the pulses, the electrical stimulation intensity can be adjusted. For specific treatment waveforms, known waveforms may be utilized. Note that the treatment waveform may be an alternating current waveform rather than a pulse waveform.

The display 260 is constituted of, for example, a liquid crystal display (LCD) and displays various information in accordance with an instruction from the processor 210.

Treatment Current

Figure 5:
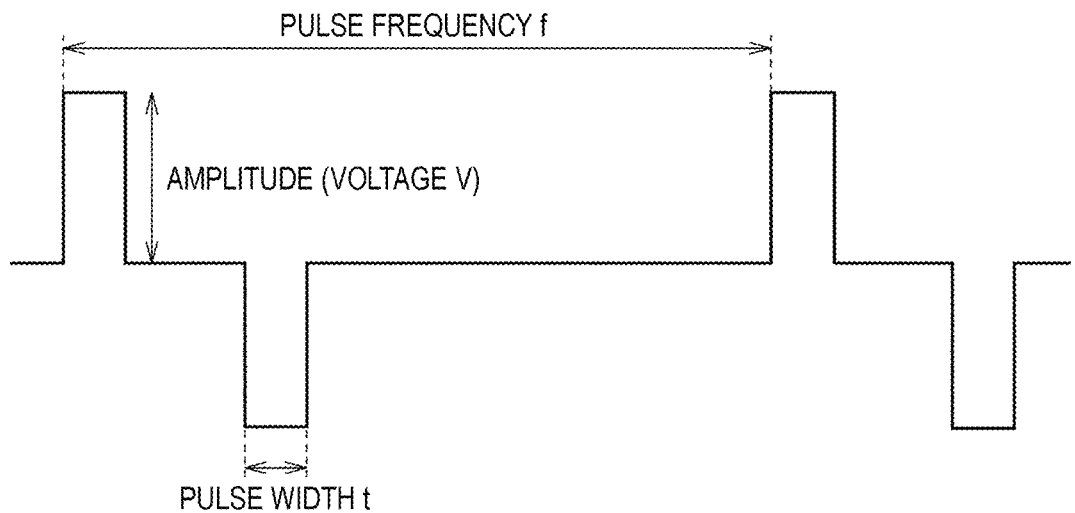
FIG. 5 is a diagram illustrating parameters of a treatment waveform.

FIG. 5 is a diagram illustrating an example of a treatment current output by the low-frequency treatment device 200. Referring to FIG. 5, a treatment waveform of the present embodiment will be described. As illustrated in FIG. 5, the parameters of the treatment waveform include an amplitude (voltage V), a pulse width t, and a pulse frequency f. The processor 210 can change the treatment for the user (can change the electrical stimulation intensity) by changing at least one parameter of the three parameters.

Processing of Low-Frequency Treatment Device 200

Figure 6:
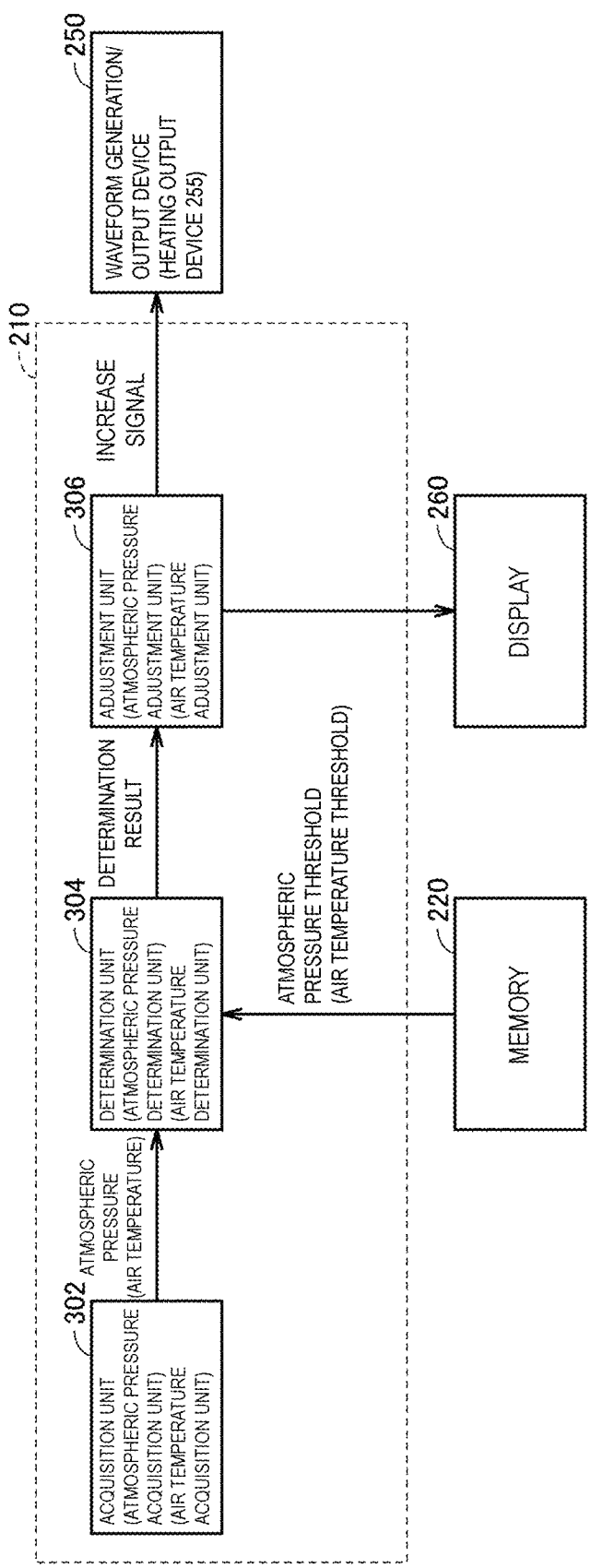
FIG. 6 is a diagram illustrating an example of the functional configuration of a processor 210.

FIG. 6 is a diagram illustrating an example of the functional configuration of the processor 210. Referring to FIG. 6, the functions of the processor 210 will be described. An acquisition unit 302 acquires a weather parameter for the position where the low-frequency treatment device 200 is located. The weather parameter may cause an increase in the pain affecting the body of the user. Typically, when the atmospheric pressure at the position of the user decreases, shoulder stiffness, joint pain, and the like (also referred to below as "body pain") felt by the user has a tendency to intensify (increase). In view of this tendency, in the present embodiment, the weather parameter is defined as atmospheric pressure. As described above, in the first embodiment, the acquisition unit 302 functions as an atmospheric pressure acquisition unit that acquires the atmospheric pressure. In the present embodiment, the acquisition unit 302 acquires position information indicating the position of the low-frequency treatment device 200. The acquisition unit 302 acquires the position information using the Global Positioning System (GPS), for example. The acquisition unit 302 sends the position information to the weather server 30 via the communication interface 245 and the network 41. The weather server 30 receives the position information and extracts the atmospheric pressure corresponding to the position information specified in the table 32 closest to the received position information or the atmospheric pressure corresponding to the position information specified in the table 32 that matches the received position information. The weather server 30 sends the extracted atmospheric pressure as atmospheric pressure information to the low-frequency treatment device 200. The acquisition unit 302 acquires the sent atmospheric pressure information via the network 41 and the communication interface 245.

The acquisition unit 302 sends the atmospheric pressure information to a determination unit 304. An atmospheric pressure threshold is stored in the memory 220. In the present embodiment, the atmospheric pressure threshold is a predetermined value. The determination unit 304 determines whether the atmospheric pressure indicated by the atmospheric pressure information sent from the acquisition unit 302 is lower than the atmospheric pressure threshold stored in the memory 220. In this way, the determination unit 304 functions as an atmospheric pressure determination unit that determines the magnitude of the atmospheric pressure acquired by the acquisition unit 302.

The determination unit 304 outputs the determination result to the adjustment unit 306. The adjustment unit 306 analyzes the determination result. When the result is that the atmospheric pressure acquired by the acquisition unit 302 is less than the atmospheric pressure threshold, the adjustment unit 306 adjusts the intensity of the low frequency treatment to increase the intensity of the low frequency treatment. In the present embodiment, the adjustment unit 306 outputs an increase signal to the waveform generation/output device 250. The increase signal is a signal for increasing the intensity (for example, electrical stimulation intensity) of the low frequency treatment performed by the pads 270. By outputting the increase signal, the waveform generation/output device 250 changes the intensity of the low frequency treatment performed by the pads 270 to a treatment waveform (also referred to below as "increased treatment waveform") that provides a higher intensity low frequency treatment performed by the pads 270.

Figure 7:
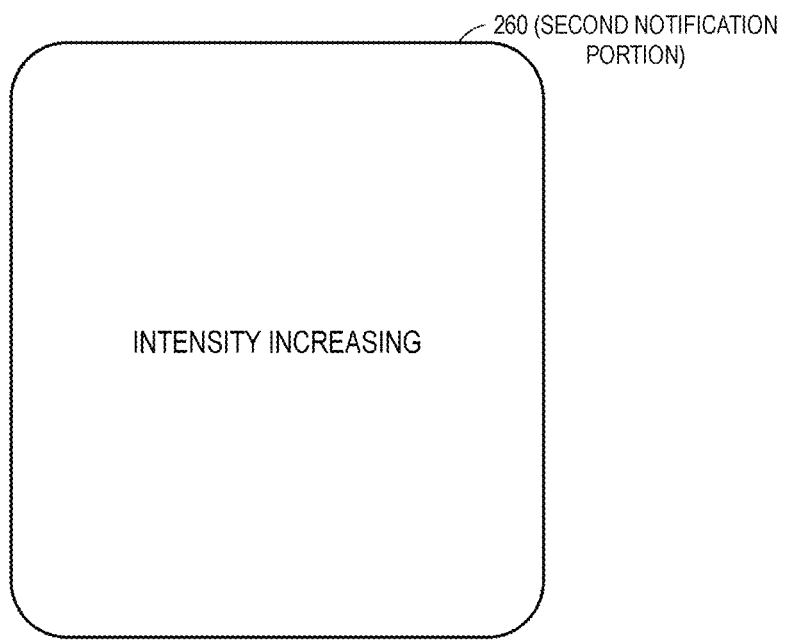
FIG. 7 is a diagram illustrating a second notification portion.

When the waveform generation/output device 250 changes the treatment waveform to the increased treatment waveform, information saying that the increased treatment waveform will be changed to is displayed on the display 260. FIG. 7 is a diagram illustrating an example of information saying that the increased treatment waveform will be changed to. In the example of FIG. 7, the "information saying that the increased treatment waveform will be changed to" is notified of via a second notification portion using the characters "intensity increasing". Hereinafter, the processing of displaying such characters is referred to as "increasing notification".

Figure 8:
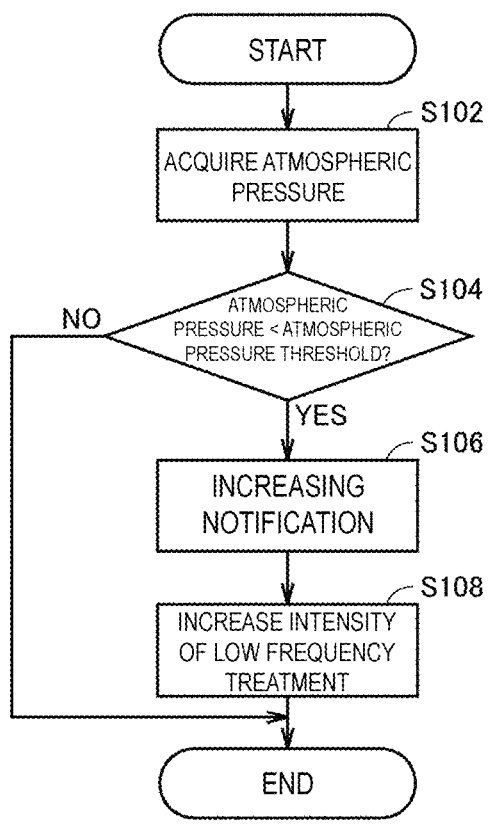
FIG. 8 is a diagram illustrating a flowchart relating to the low-frequency treatment device.

FIG. 8 is a diagram illustrating a flowchart relating to the low-frequency treatment device 200. Referring to FIG. 8, the flowchart relating to the low-frequency treatment device 200 will be described. The flowchart of FIG. 8 and the flowchart described below start when the low-frequency treatment device 200 is powered ON.

First, in step S102, the acquisition unit 302 acquires the position where the low-frequency treatment device 200 is located or the atmospheric pressure near the position from the weather server 30.

Next, in step S104, the determination unit 304 determines whether the atmospheric pressure acquired by the acquisition unit 302 is less than the atmospheric pressure threshold. If the atmospheric pressure acquired by the acquisition unit 302 is equal to or greater than the atmospheric pressure threshold (NO in step S104), the processing ends. If the atmospheric pressure acquired by the acquisition unit 302 is less than the atmospheric pressure threshold (YES in step S104), the processing moves to step S106.

In step S106, the adjustment unit 306 causes the display 260 to execute the increasing notification (see FIG. 7). When the processing of step S106 ends, the processing of the processor 210 moves to step S108.

In step S108, the adjustment unit 306 changes the treatment waveform to the increased treatment waveform and increases the intensity of the low frequency treatment.

The processing of FIG. 8 is repeated a second time and so on every predetermined amount of time (for example, every minute). Also, the processing of FIG. 8 is not executed in the case where the processing of step S108 has been executed. For example, in the case where the processing of step S108 has been executed, a finished adjustment flag indicating that adjustment of the low frequency treatment has been executed is stored in a predetermined region. The predetermined region is RAM in the memory 220, for example. In the case where this finished adjustment flag is stored, the processing of FIG. 8 is not executed. In the case where the low-frequency treatment device 200 is powered off, for example, the finished adjustment flag is erased.

Next, the effects of the low-frequency treatment device 200 of the present embodiment will be described. Typically, when the atmospheric pressure at the position of the user decreases, body pain felt by the user has a tendency to intensify. In view of this tendency, the low-frequency treatment device 200 of the present embodiment can increase the intensity of the low frequency treatment when the atmospheric pressure of the position where the low-frequency treatment device 200 is located is less than the atmospheric pressure threshold. This removes the need for a user receiving low frequency treatment via the low-frequency treatment device 200 to increase the intensity of the low frequency treatment when the atmospheric pressure goes below the atmospheric pressure threshold. Because the low-frequency treatment device 200 can increase the intensity of the low frequency treatment, user convenience is enhanced.

Also, when the increased treatment waveform is changed to, at least one of the three parameters described in relation to FIG. 5 (amplitude, pulse width, pulse frequency) is changed. Preferably, the low-frequency treatment device 200 executes processing to increase the amplitude of the waveform of the treatment current as the processing to increase the intensity of the low frequency treatment. This is because when a parameter other than the amplitude is changed, the user may feel discomfort. By increasing the value for the amplitude, the low-frequency treatment device 200 can increase the intensity of the low frequency treatment without causing discomfort to the user.

Also, as described in step S106 of FIG. 8, the increasing notification is executed before the intensity of the low frequency treatment is increased. The increasing notification can make the user aware in advance of the increase in intensity of the low frequency treatment. Thus, it is possible to prevent the user from unintentionally increasing the intensity of the low frequency treatment.

Second Embodiment

For some users, treating a pain-affected region with heat treatment relieves pain more than low frequency treatment. The low-frequency treatment device 200 according to a second embodiment can execute low frequency treatment and heat treatment. The user can select a low frequency treatment mode or a heat treatment mode via operation of the operation interface 230, for example. Also, a heating member is embedded in a pad according to the second embodiment. The heating member is, for example, a coil that emits heat.

Figures 9, 10:
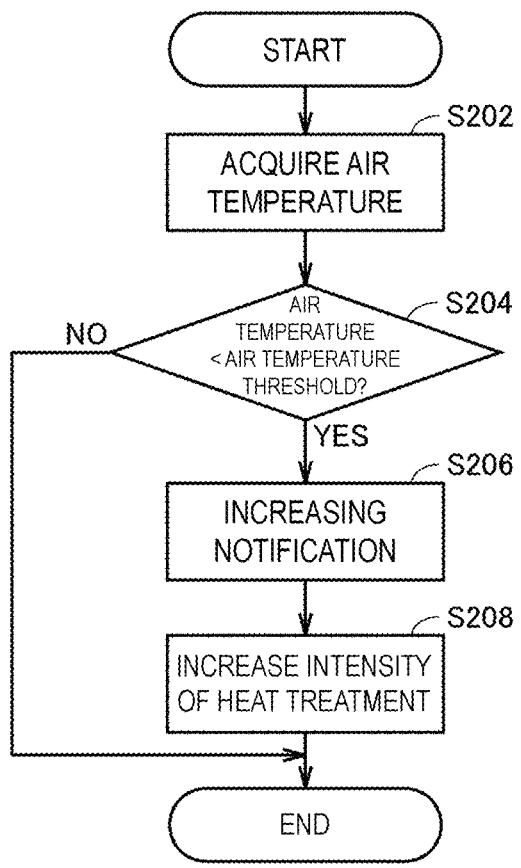
FIG. 9 is a diagram illustrating an example of a table.
FIG. 10 is a diagram illustrating a flowchart relating to the low-frequency treatment device.

Also, in the second embodiment, temperature is used as a weather parameter that causes an increase of body pain of the user. In the second embodiment, the weather server 30 includes a table 34 (see FIG. 1) that includes position information and air temperature information of positions specified by the position information associated together. FIG. 9 illustrates an example of the table 34. In the example of FIG. 9, the position information includes longitude X1 and latitude Y1, and the associated air temperature is W1 (degrees). This means that the air temperature at a position with the longitude X1 and the latitude Y1 is W1 (degrees). The weather server 30 repeatedly updates the air temperature information specified in the table 34 with the latest air temperature information every predetermined amount of time (for example, every hour).

Referring to FIG. 6, an example of the functional configuration of the processor 210 of the low-frequency treatment device 200 of the second embodiment will be described. An acquisition unit 302 acquires the air temperature (temperature) for the position where the low-frequency treatment device 200 is located. As described above, in the second embodiment, the acquisition unit 302 functions as an air temperature acquisition unit that acquires the air temperature. In the present embodiment, the acquisition unit 302 acquires position information indicating the position of the low-frequency treatment device 200. The acquisition unit 302 acquires the position information using the Global Positioning System (GPS), for example. The acquisition unit 302 sends the position information to the weather server 30 via the communication interface 245 and the network 41. The weather server 30 receives the position information and extracts the air temperature corresponding to the position information specified in the table 34 closest to the received position information or the air temperature corresponding to the position information specified in the table 34 that matches the received position information. The weather server 30 sends the extracted air temperature as air temperature information to the low-frequency treatment device 200. The acquisition unit 302 acquires the sent air temperature information via the network 41 and the communication interface 245.

The acquisition unit 302 sends the air temperature information to the determination unit 304. An air temperature threshold is stored in the memory 220. This air temperature threshold is a predetermined value. The determination unit 304 determines whether the air temperature indicated by the air temperature information sent from the acquisition unit 302 is lower than the air temperature threshold stored in the memory 220. In this way, the determination unit 304 functions as an air temperature determination unit that determines the magnitude of the air temperature acquired by the acquisition unit 302.

The determination unit 304 outputs the determination result to the adjustment unit 306. The adjustment unit 306 analyzes the determination result. When the result is that the air temperature acquired by the acquisition unit 302 is less than the air temperature threshold, an increase signal is output to the waveform generation/output device 250. The increase signal is a signal for increasing the intensity of the heat treatment performed by the pads 270. By outputting the increase signal, a heating output device 255 increases the temperature of the coils in the pads 270. This increases the temperature of the pads 270. An example of a technique to increase coil temperature includes increasing the current running through the coils and increasing the coil temperature.

Also, when the temperature of the pads 270 is increased by the heating output device 255, information saying that the temperature of the pads 270 will increase is displayed on the display 260. Although not illustrated, as information saying that the temperature of the pads 270 will increase, the characters "temperature increasing" may be displayed.

FIG. 10 is a diagram illustrating a flowchart relating to the low-frequency treatment device 200. Referring to FIG. 10, the flowchart relating to the low-frequency treatment device 200 will be described.

First, in step S202, the acquisition unit 302 acquires the air temperature where the low-frequency treatment device 200 is located from the weather server 30.

Next, in step S204, the determination unit 304 determines whether the air temperature acquired by the acquisition unit 302 is less than the air temperature threshold. If the air temperature acquired by the acquisition unit 302 is equal to or greater than the air temperature threshold (NO in step S204), the processing ends. If the air temperature acquired by the acquisition unit 302 is less than the air temperature threshold (YES in step S204), the processing moves to step S206.

In step S206, the adjustment unit 306 causes the display 260 to execute the increasing notification (a notification of information saying that the temperature of the pads 270 will increase). When the processing of step S206 ends, the processing of the processor 210 moves to step S208.

In step S208, the adjustment unit 306 increases the intensity of the heat treatment, that is, increases the temperature of the pads 270.

Also, the processing of FIG. 10 is repeated a second time and so on every predetermined amount of time (for example, every minute). Also, the processing of FIG. 10 is not executed in the case where the processing of step S208 has been executed. For example, in the case where the processing of step S208 has been executed, a finished adjustment flag indicating that adjustment of the heat treatment has been executed is stored in a predetermined region. The predetermined region is RAM in the memory 220, for example. In the case where this finished adjustment flag is stored, the processing of FIG. 10 is not executed. In the case where the low-frequency treatment device 200 is powered off, for example, the finished adjustment flag is erased.

Next, the effects of the low-frequency treatment device 200 of the second embodiment will be described. The low-frequency treatment device 200 of the second embodiment can increase the intensity of the low frequency treatment when the air temperature of the position where the low-frequency treatment device 200 is located is less than the air temperature threshold. This removes the need for a user receiving heat treatment via the low-frequency treatment device 200 to increase the intensity of the heat treatment when the air temperature goes below the air temperature threshold. Because the low-frequency treatment device 200 can increase the intensity of the heat treatment, user convenience is enhanced.

Also, as described in step S206 of FIG. 10, the increasing notification is executed before the intensity of the heat treatment is increased. The increasing notification can make the user aware in advance of the increase in intensity of the heat treatment. Thus, it is possible to prevent the user from unintentionally increasing the intensity of the heat treatment.

Third Embodiment

Next, a third embodiment will be described. In the third embodiment, when the atmospheric pressure is determined to decrease below an atmospheric pressure threshold in the future, the low-frequency treatment device 200 causes the display 260 to notify saying to refrain from going outside in the time period when the atmospheric pressure is less than the atmospheric pressure threshold.

Figures 11, 12:
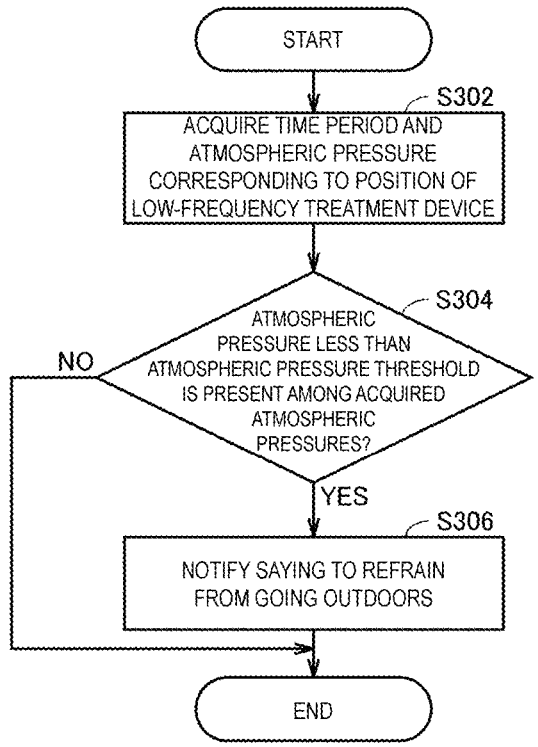
FIG. 11 is a diagram illustrating an example of a table.
FIG. 12 is a diagram illustrating a flowchart relating to the low-frequency treatment device.

Also, in the third embodiment, the weather server 30 includes a table 36 that includes position information, time periods for each position information, and the atmospheric pressure in the time periods associated together. FIG. 11 illustrates an example of the table 36. The position information in the example of FIG. 2 includes a longitude X and a latitude Y. Also, the time periods are split into units of a predetermined amount of time (for example, one hour). "Predetermined amount of time" may refer to any amount of time and, for example, may be a period during which the user is expected to be outdoors. The period during which the user is expected to be outdoors may be, for example, the time from 6 AM to 12 midnight.

In the example of FIG. 11, Z1 (hPa) is associated with the time period T1 to T2 (time period of one hour) for the position information with the longitude X1 and the latitude Y1, and Z2 (hPa) is associated with the time period T2 to T3 (time period of one hour) for the position information with the longitude X1 and the latitude Y1. Similarly, Z3 (hPa) is associated with the time period T1 to T2 (time period of one hour) for the position information with the longitude X2 and the latitude Y2, and Z4 (hPa) is associated with the time period T2 to T3 (time period of one hour) for the position information with the longitude X2 and the latitude Y2. Also relating to the position information, the atmospheric pressure is specified for other times. Furthermore, time periods and atmospheric pressures are specified for other position information.

The table 36 of FIG. 11 includes the forecast atmospheric pressure for each time period of one day. The weather server 30 acquires weather forecast data from a predetermined institution (for example, a meteorological agency) at a predetermined time of a day (for example, 1 AM). The table 36 of FIG. 11 is formed from this data.

FIG. 12 is a diagram illustrating a flowchart relating to the low-frequency treatment device 200 of the third embodiment. Referring to FIG. 12, the flowchart relating to the low-frequency treatment device 200 will be described.

When the low-frequency treatment device 200 is powered ON, the low-frequency treatment device 200 sends position information. The weather server 30 receives the sent position information and extracts time periods and atmospheric pressures corresponding to the position information closest to the received position information specified in the table 36 (or position information that matches the received position information).

The weather server 30 sends the time periods and the atmospheric pressures to the low-frequency treatment device 200. In step S302, the processor 210 acquires the sent time periods and the atmospheric pressures. Next, the processor 210 determines whether an atmospheric pressure equal to or below the atmospheric pressure threshold is present among the acquired atmospheric pressures. If it is determined that an atmospheric pressure equal to or below the atmospheric pressure threshold is present among the acquired atmospheric pressures, this means that a time period with an atmospheric pressure equal to or less than the atmospheric pressure threshold is present on the day which the processing of FIG. 12 was executed.

If YES is determined in step S304, the processing of the processor 210 moves to step S306. If NO is determined in step S304, the processing of the processor 210 ends.

In step S306, the time of the beginning of the time period corresponding to the atmospheric pressure equal to or less than the atmospheric pressure threshold is extracted and a time X from the current time to the extracted time (time when the atmospheric pressure is equal to or less than the atmospheric pressure threshold) is calculated. After the time X is calculated, the processor 210 causes the display 260 to notify of information saying "Refrain from going outdoors in X time". In this way, in a case where the atmospheric pressure is determined to decrease below an atmospheric pressure threshold (in the future), the display 260, functioning as a first notification portion, notifies saying to refrain from going outside in the time period when the atmospheric pressure is less than the atmospheric pressure threshold.

Figure 13:
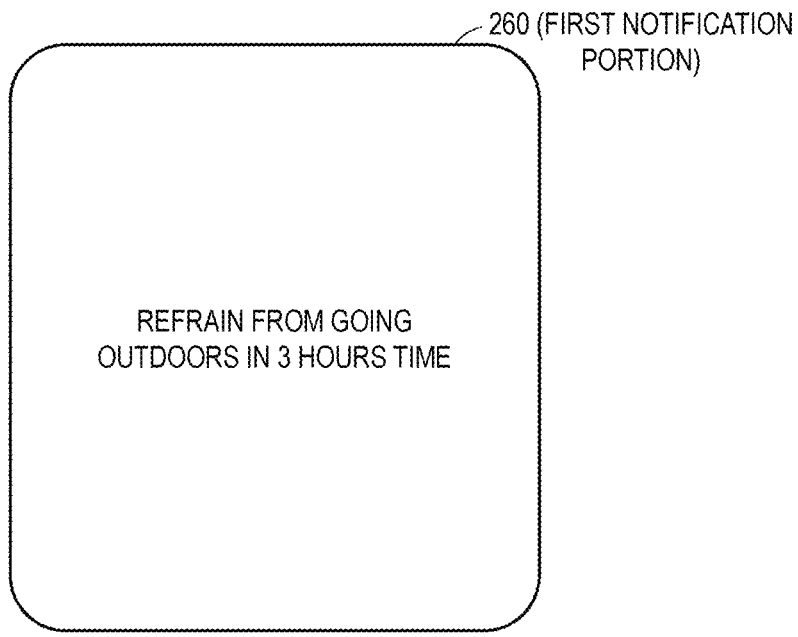
FIG. 13 is a diagram illustrating a first notification portion.

When the user is notified, the user can confirm that the atmospheric pressure will reach the atmospheric pressure threshold in X time and that he/she should refrain from going outdoors in X time. FIG. 13 illustrates an example notification on the display 260 for when the calculated time is three hours. The user can confirm that the atmospheric pressure will reach the atmospheric pressure threshold in three hours time and that he/she should refrain from going outdoors in three hours time.

By a notification such as that illustrated in FIG. 13, the low-frequency treatment device 200 can minimize or prevent body pain of the user increasing when outdoors due to the atmospheric pressure reaching the atmospheric pressure threshold. The notification is not limited to that illustrated in FIG. 13 and may include the time period. For example, the notification may say "Refrain from going outdoors between 1 PM and 3 PM".

Next, a modified example of the third embodiment will be described. As in the description of FIG. 12, the low-frequency treatment device 200 acquires the time periods and atmospheric pressures sent from the weather server 30 in step S302 and determines whether an atmospheric pressure equal to or less than the atmospheric pressure threshold is present among the received atmospheric pressures in step S304. However, the weather server 30 may perform the determination of step S304. That is, the low-frequency treatment device 200 may send position information and the atmospheric pressure threshold to the weather server 30. After the weather server 30 receives the position information and the atmospheric pressure threshold, the weather server 30 determines whether an atmospheric pressure threshold corresponding to the position information is present. In other words, the weather server 30 executes determination processing corresponding to step S304. In a case where the weather server 30 determines that an atmospheric pressure threshold corresponding to the position information is present, the time period corresponding to the atmospheric pressure threshold is sent. Then, the low-frequency treatment device 200 executes the processing of step S306. In a case where the weather server 30 determines that an atmospheric pressure threshold corresponding to the position information is not present, the weather server 30 sends information saying it is not present to the low-frequency treatment device 200. When this information is received, the low-frequency treatment device 200 does not execute the processing of step S306. A treatment system employing such a modified example has similar effects to that of the third embodiment.

Fourth Embodiment

Next, a fourth embodiment will be described. In the fourth embodiment, the concept "atmospheric pressure" in the description of the third embodiment is replaced with "air temperature". In other words, in the fourth embodiment, when the air temperature is determined to decrease below an air temperature threshold in the future, the low-frequency treatment device 200 causes the display 260 to notify saying to refrain from going outside in the time period when the air temperature is less than the air temperature threshold.

In the fourth embodiment, for example, "atmospheric pressure" of the table 36 of FIG. 11 is replaced with "air temperature" and "atmospheric pressure" of FIG. 12 is replaced with "air temperature". Also, "atmospheric pressure threshold" is replaced with "air temperature threshold".

In the fourth embodiment, if the air temperature is determined to decrease below an air temperature threshold (in the future), the display 260, functioning as a first notification portion, notifies saying to refrain from going outside in the time period when the air temperature is less than the air temperature threshold.

When the user is notified, the user can confirm that the air temperature will reach the air temperature threshold in X time and that he/she should refrain from going outdoors in X time. FIG. 13 illustrates an example notification on the display 260 for when the calculated time is three hours. The user can confirm that the air temperature will reach the air temperature threshold in three hours time and that he/she should refrain from going outdoors in three hours time.

By a notification such as that illustrated in FIG. 13, the low-frequency treatment device 200 can minimize or prevent body pain of the user increasing when outdoors due to the air temperature reaching the air temperature threshold.

Fifth Embodiment

Next, a fifth embodiment will be described. In the fifth embodiment, in a case where the atmospheric pressure is determined to be less than the atmospheric pressure threshold, the low-frequency treatment device 200 notifies of a treatment facility near where the low-frequency treatment device 200 is located. A treatment facility is, for example, a facility for treating the body pain of a user.

Figure 14:
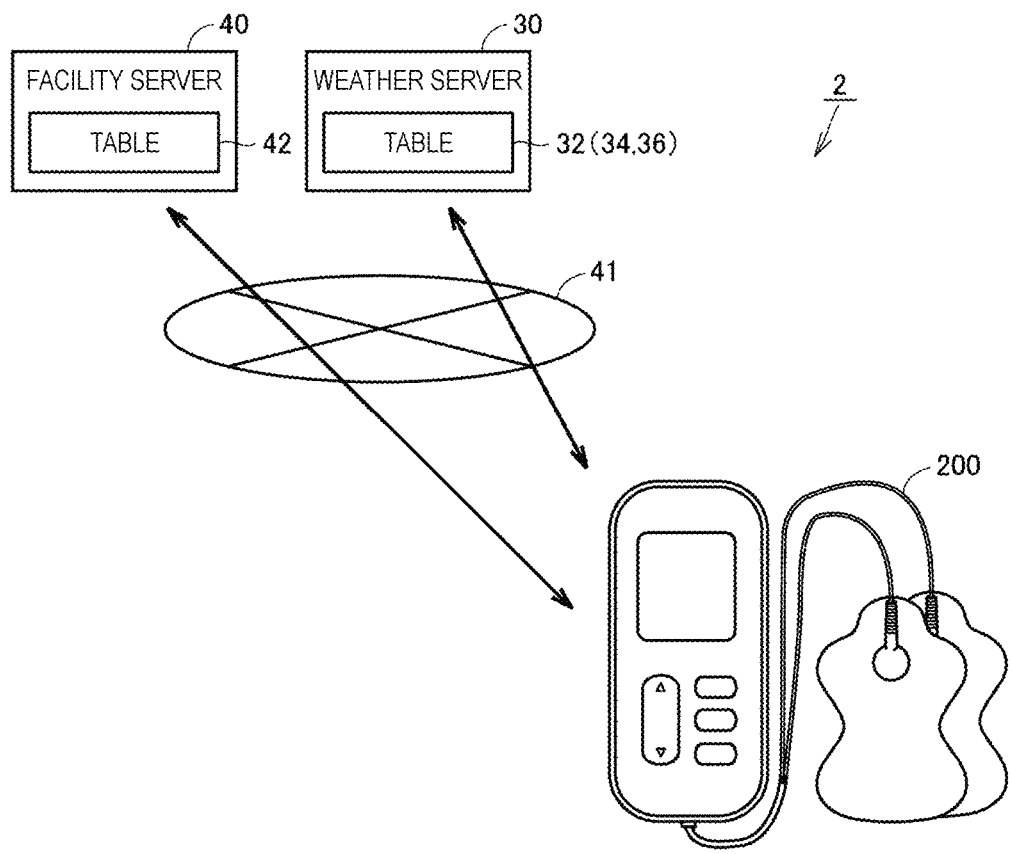
FIG. 14 is a diagram illustrating a schematic configuration of a treatment system 2.

FIG. 14 is a diagram illustrating a schematic configuration of a treatment system 2 according to a fifth embodiment. Comparing FIG. 14 with FIG. 1, the configuration of FIG. 14 differs from that of FIG. 1 in that it further includes a facility server 40. The facility server 40 includes a table 42. The table 42 specifies information including position information and treatment facilities specified from the position information associated together.

Figures 15, 16:
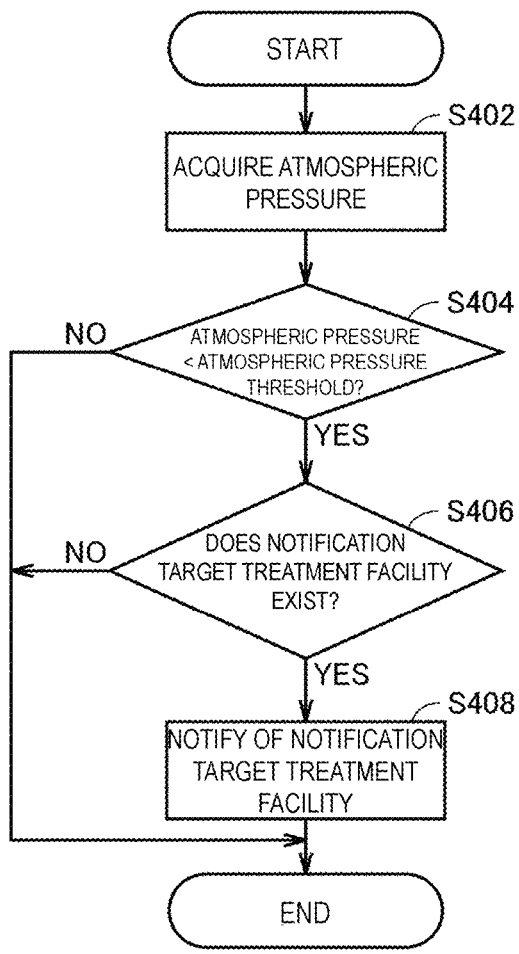
FIG. 15 is a diagram illustrating an example of a table.
FIG. 16 is a diagram illustrating a flowchart relating to the low-frequency treatment device.

FIG. 15 illustrates an example of the table 42. The position information in the example of FIG. 15 includes a longitude and a latitude. In the example of FIG. 15, the position information, treatment information indicating the treatment facility at the position indicated by the position information, and treatment content that the treatment facility can provide are associated together. For example, at the position with longitude X11 and latitude Y11, a treatment facility CC of BB city, AA prefecture is located, and the treatment content available at the facility CC is indicated to be low frequency treatment and heat treatment.

FIG. 16 is a diagram illustrating a flowchart relating to the low-frequency treatment device 200 of the fifth embodiment. Referring to FIG. 16, the flowchart relating to the low-frequency treatment device 200 will be described. Steps S402 and S404 are the same as steps S102 and S104 of FIG. 8. If YES is determined in step S404, i.e., the atmospheric pressure is determined to be less than the atmospheric pressure threshold, the processing of the processor 210 moves to step S406.

In step S406, the processor 210 sends to the facility server 40 position information of the low-frequency treatment device 200 including the processor 210 and processing information indicating processing content that the low-frequency treatment device 200 can execute. The facility server 40 determines whether a treatment facility that can perform a treatment unable to be executed by the low-frequency treatment device 200 is located within a predetermined distance from the received position information (referred to below as "notification target treatment facility"). Here, the predetermined distance is a predetermined distance and, in some embodiments, is the distance that a user with body pain can move without burdening the body. Also, in regards to "a treatment facility that can perform a treatment unable to be executed by the low-frequency treatment device 200", in the case where the low-frequency treatment device 200 cannot execute heat treatment, the "treatment unable to be executed by the low-frequency treatment device 200" refers to "heat treatment".

In a case where the facility server 40 determines that the notification target treatment facility exists, the facility server 40 sends to the low-frequency treatment device 200 facility information indicating the name, address, and the like of the notification target treatment facility. In a case where the facility server 40 determines that the notification target treatment facility does not exist, the facility server 40 sends to the low-frequency treatment device 200 information saying that a notification target treatment facility does not exist.

The low-frequency treatment device 200 determines YES for step S406 if facility information is received. The low-frequency treatment device 200 determines NO for step S406 if information saying that a notification target treatment facility does not exist is received. If NO is determined in step S406, the processing of FIG. 16 ends. If YES is determined in step S406, the processing moves to step S408.

Figure 17:
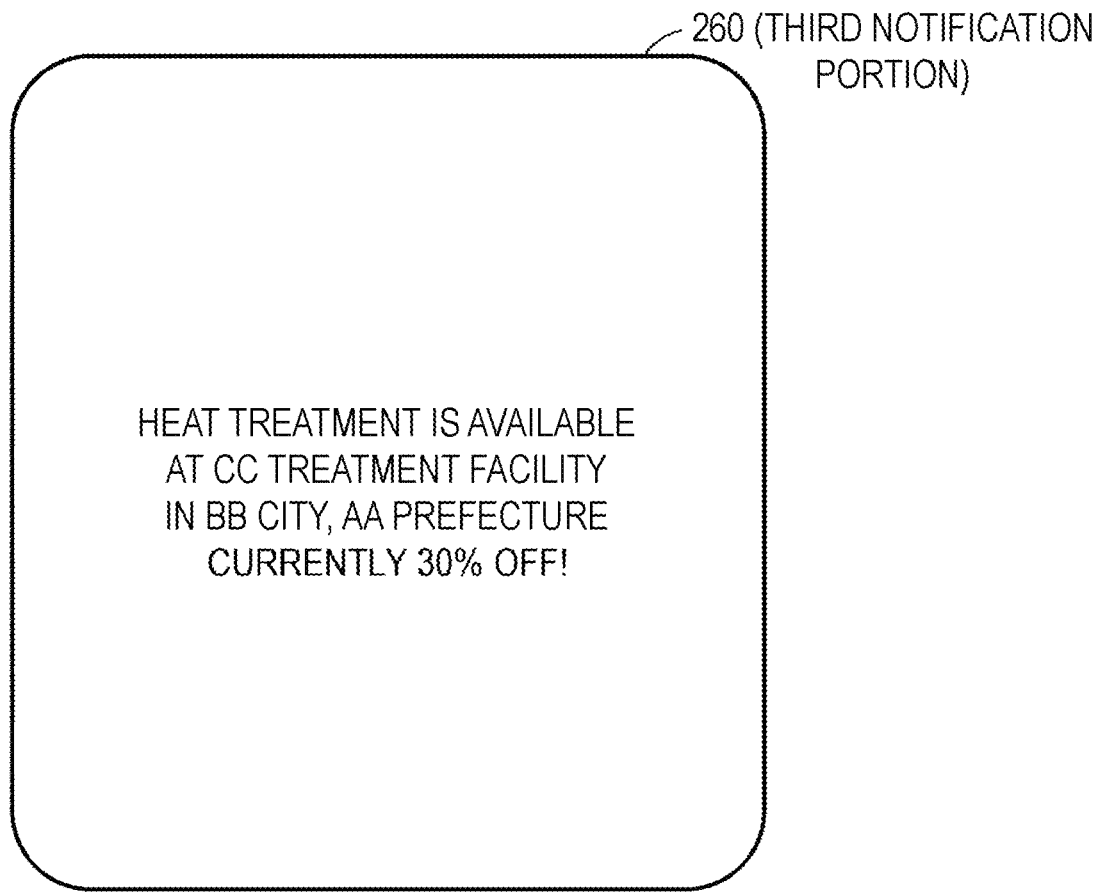
FIG. 17 is a diagram illustrating a third notification portion.

In step S408, upon the control of the processor 210, the display 260, functioning as a third notification portion, notifies of a treatment facility near where the low-frequency treatment device 200 is located. The notification is executed on the basis of the facility information received by the low-frequency treatment device 200. FIG. 17 illustrates an example of the notification. In the example of FIG. 17, characters saying "Heat treatment is available at CC treatment facility in BB city, AA prefecture. Currently 30% off!" are displayed on the display 260.

Also, the processing of FIG. 16 is repeated a second time and so on every predetermined amount of time (for example, every minute). Also, the processing of FIG. 16 is not executed in the case where the processing of step S408 has been executed. For example, in the case where the processing of step S408 has been executed, a finished notification flag indicating that notification of the treatment facility has been executed is stored in a predetermined region. The predetermined region is RAM in the memory 220, for example. In the case where this finished notification flag is stored, the processing of FIG. 16 is not executed. In the case where the low-frequency treatment device is powered off, for example, the finished notification flag is erased.

In this way, the low-frequency treatment device 200 can promote treatment at a treatment facility to the user via notifications such as that illustrated in FIG. 17. Also, the user can be made aware of treatment facilities near where his/her low-frequency treatment device 200 is located. Furthermore, via the notification of FIG. 17, the user can be made aware of treatment facilities that can provide treatment that his/her low-frequency treatment device 200 cannot execute. As illustrated in FIG. 17, the notification may also include information about treatment cost discounts. Thus, the user can be made aware that his/her can receive treatment at a discounted treatment cost.

As a modified example of the fifth embodiment, the notification target treatment facility may be notified of via the display 260, and the treatment content that the low-frequency treatment device 200 cannot execute and the treatment cost may not be notified of. In this case, for example, when the atmospheric pressure is less than the atmospheric pressure threshold and the body pain of the user is expected to increase, the user may desire to receive low frequency treatment at a treatment facility rather than receive low frequency treatment via his/her low-frequency treatment device 200. In this case, even if the notification target treatment facility is notified of via the display 260, and the treatment content that the low-frequency treatment device 200 cannot execute and the treatment cost are notified of, by making the user aware of the notification target treatment facility, treatment at the notification target treatment facility can be promoted to the user. The user can also be made aware that they can receive low frequency treatment at the treatment facility.

As another modified example of the fifth embodiment, instead of using atmospheric pressure and an atmospheric pressure threshold in step S402 and step S404 of FIG. 16, air temperature and an air temperature threshold may be used in step S402 and step S404. That is, step S202 and step S204 of FIG. 10 may be replaced by step S402 and step S404. A treatment system employing such a configuration has similar effects to that of the fifth embodiment.

Sixth Embodiment

As described above, in the first embodiment, only one atmospheric pressure threshold is used. In the sixth embodiment, the atmospheric pressure threshold includes two atmospheric pressure thresholds, i.e., a first atmospheric pressure threshold and a second atmospheric pressure threshold. Also, the second atmospheric pressure threshold is greater than the first atmospheric pressure threshold.

In the sixth embodiment, the atmospheric pressure threshold described in the first embodiment (see step S104 of FIG. 8) is defined as the first atmospheric pressure threshold, and the second atmospheric pressure threshold will be described below. Referring to FIG. 6, the functional configuration of the processor 210 according to the sixth embodiment will be described.

In the sixth embodiment, if the atmospheric pressure acquired by the atmospheric pressure acquisition unit is determined to be less than the first atmospheric pressure threshold, the intensity of the low frequency treatment is increased. As described in the description of the first embodiment, this removes the need for a user receiving low frequency treatment via the low-frequency treatment device 200 to increase the intensity of the low frequency treatment when the atmospheric pressure goes below the atmospheric pressure threshold. Because the low-frequency treatment device 200 can increase the intensity of the low frequency treatment, user convenience is enhanced.

If the atmospheric pressure acquired by the atmospheric pressure acquisition unit is determined to be greater than the second atmospheric pressure threshold, the intensity of the low frequency treatment is decreased. This can reduce the power consumption of the low-frequency treatment device.

Figure 18:
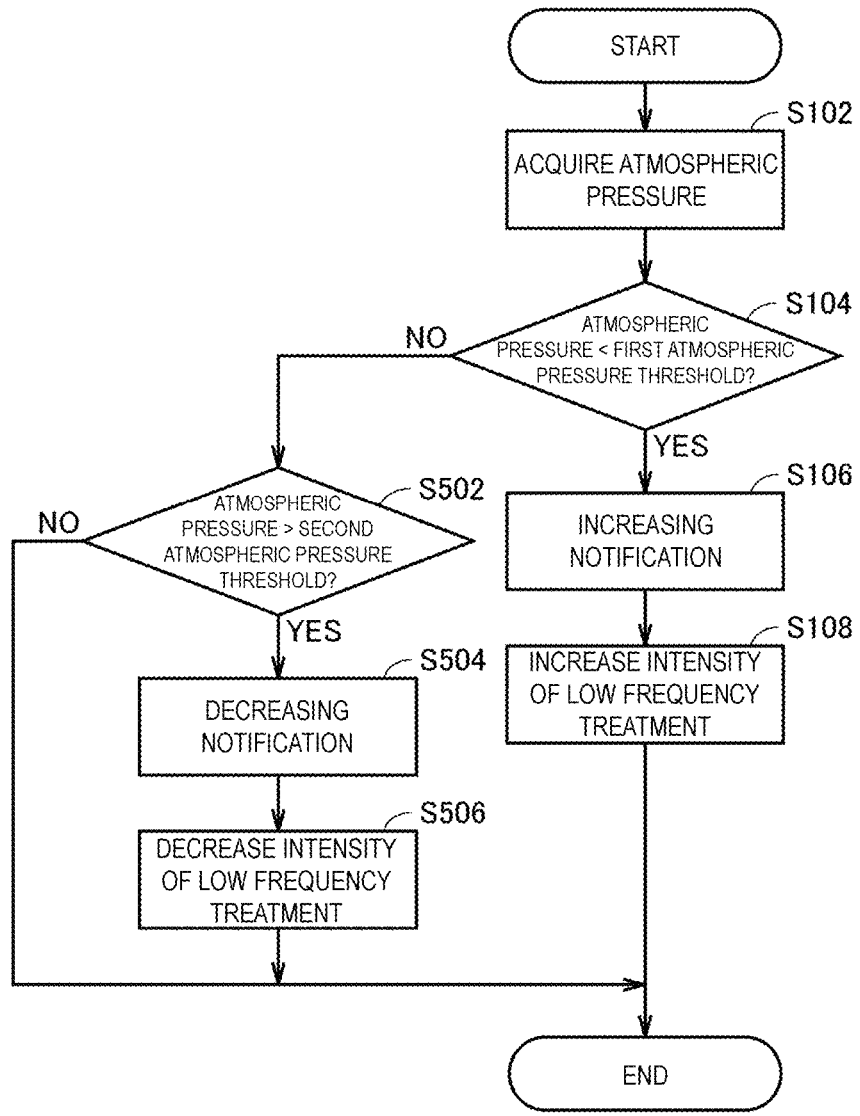
FIG. 18 is a diagram illustrating a flowchart relating to the low-frequency treatment device.

FIG. 18 is a diagram illustrating a flowchart of the sixth embodiment. In step S104, the determination unit 304 determines whether the atmospheric pressure acquired by the acquisition unit 302 is less than the first atmospheric pressure threshold. If the atmospheric pressure acquired by the acquisition unit 302 is determined to be less than the first atmospheric pressure threshold (YES in step S104), the processing of the processor 210 moves to step S106. If the atmospheric pressure acquired by the acquisition unit 302 is determined to be not less than the first atmospheric pressure threshold (NO in step S104), the processing of the processor 210 moves to step S502.

In step S502, the determination unit 304 determines whether the atmospheric pressure acquired by the acquisition unit 302 is greater than the second atmospheric pressure threshold. If the atmospheric pressure acquired by the acquisition unit 302 is determined to be greater than the second atmospheric pressure threshold (YES in step S502), the processing moves to step S504. If NO is determined in step S502, the processing ends. In step S504, the adjustment unit 306 causes the display 260 to execute the decreasing notification (not illustrated). Here, the decreasing notification is a notification saying that the intensity of the low frequency treatment will decrease. The decreasing notification is, for example, a notification saying "intensity decreasing".

When the processing of step 504 ends, the processing of the processor 210 moves to step S506. In step S506, the adjustment unit 306 executes processing to decrease the intensity of the low frequency treatment. The processing includes, for example, sending a decrease signal to the waveform generation/output device 250. The decrease signal is a signal for decreasing the intensity (for example, electrical stimulation intensity) of the low frequency treatment performed by the pads 270. When the decrease signal is received, the waveform generation/output device 250 decreases the electrical stimulation intensity by changing at least one of the three parameters (amplitude (voltage V), pulse width t, and pulse frequency f). Also, the processing of FIG. 18 is repeated a second time and so on every predetermined amount of time (for example, every minute).

The low-frequency treatment device of the sixth embodiment adjusts the intensity of the low frequency treatment on the basis of the weather parameter (atmospheric pressure) and a predetermined threshold. For example, in step S502 to step S506 executed by the low-frequency treatment device of the sixth embodiment, in a case where the atmospheric pressure acquired by the atmospheric pressure acquisition unit is determined to be greater than the second atmospheric pressure threshold, the intensity of the low frequency treatment is decreased. This can reduce the power consumption of the low-frequency treatment device. Furthermore, by executing the processing of step S104 to step S108, the effects described in the first embodiment are achieved.

Also, as described in step S504 of FIG. 18, the decreasing notification is executed before the intensity of the low frequency treatment is decreased. The decreasing notification can make the user aware in advance of the decrease in intensity of the low frequency treatment. Thus, it is possible to prevent the user from unintentionally decreasing the intensity of the low frequency treatment.

As illustrated in FIG. 18, a modified example of the sixth embodiment may execute the processing of step S104 to step S108. That is, after the processing of step S102, the processing transitions to step S502. According to such a configuration, the processing of step S104 to step S108 may be skipped, allowing the processing burden to be reduced.

In the sixth embodiment described above, atmospheric pressure is used as a weather parameter. However, in a modified example of the sixth embodiment, air temperature is used as a weather parameter. In this modified example, the first atmospheric pressure threshold of FIG. 18 is replaced with a first air temperature threshold and the second atmospheric pressure threshold is replaced with a second air temperature threshold. Such a modified example has similar effects to that of the sixth embodiment.

Also, in the sixth embodiment described above, the treatment for which the intensity is adjusted is a "low frequency treatment". However, the treatment for which the intensity is adjusted may be a "heat treatment".

Seventh Embodiment

Figure 19:
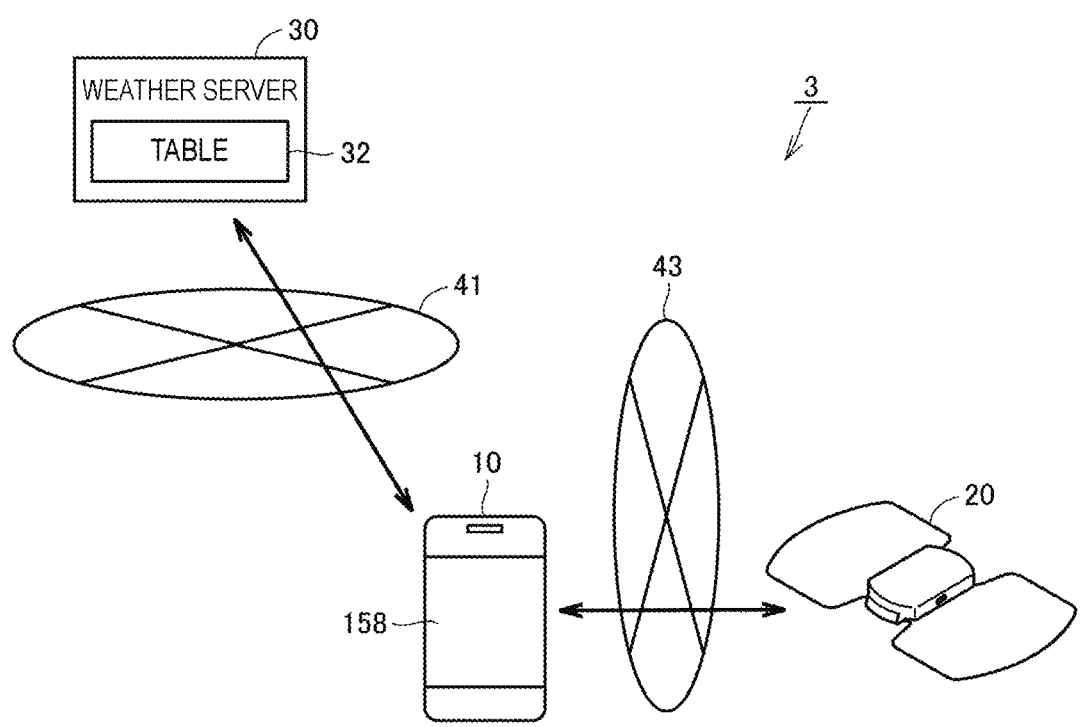
FIG. 19 is a diagram illustrating a schematic configuration of a treatment system 3.

Next, a seventh embodiment will be described. In the embodiments described above, the low-frequency treatment device 200 is a wired type. The low-frequency treatment device of the seventh embodiment is a wireless type. FIG. 19 is a diagram illustrating a schematic configuration of a treatment system 3 according to the seventh embodiment. Referring to FIG. 19, a treatment system 3 includes a terminal device 10 used by a user, a low-frequency treatment device 20, the weather server 30, and networks 41, 43. Furthermore, in the seventh embodiment, atmospheric pressure and air temperature are collectively referred to as weather parameters. Also, an atmospheric pressure threshold and an air temperature threshold are collectively referred to as thresholds. "Weather parameters are less than the thresholds" includes in its meaning both "atmospheric pressure is less than an atmospheric pressure threshold" and "air temperature is less than an air temperature threshold".

The terminal device 10 is an example of an information processing device. The terminal device 10 is, for example, a smart phone including a touch panel. Note that the terminal device 10 may be another type of terminal device such as a folding type mobile telephone, a tablet terminal device, a personal computer (PC), a personal data assistant (PDA), and the like. The terminal device 10 includes a touch panel 158 configured to display various information and receive input from the user. The touch panel 158 has the function of the display 260 and the function of the operation interface 230 illustrated in FIG. 3.

The network 43 employs a short-range wireless communication system, typically Bluetooth (trade name) low energy (BLE), to connect the terminal device 10, the low-frequency treatment device 20. However, the network 43 is not limited thereto, and a wired communication system may be employed, or other wireless communication systems such as a wireless local area network (LAN) may be employed.

Figure 20:
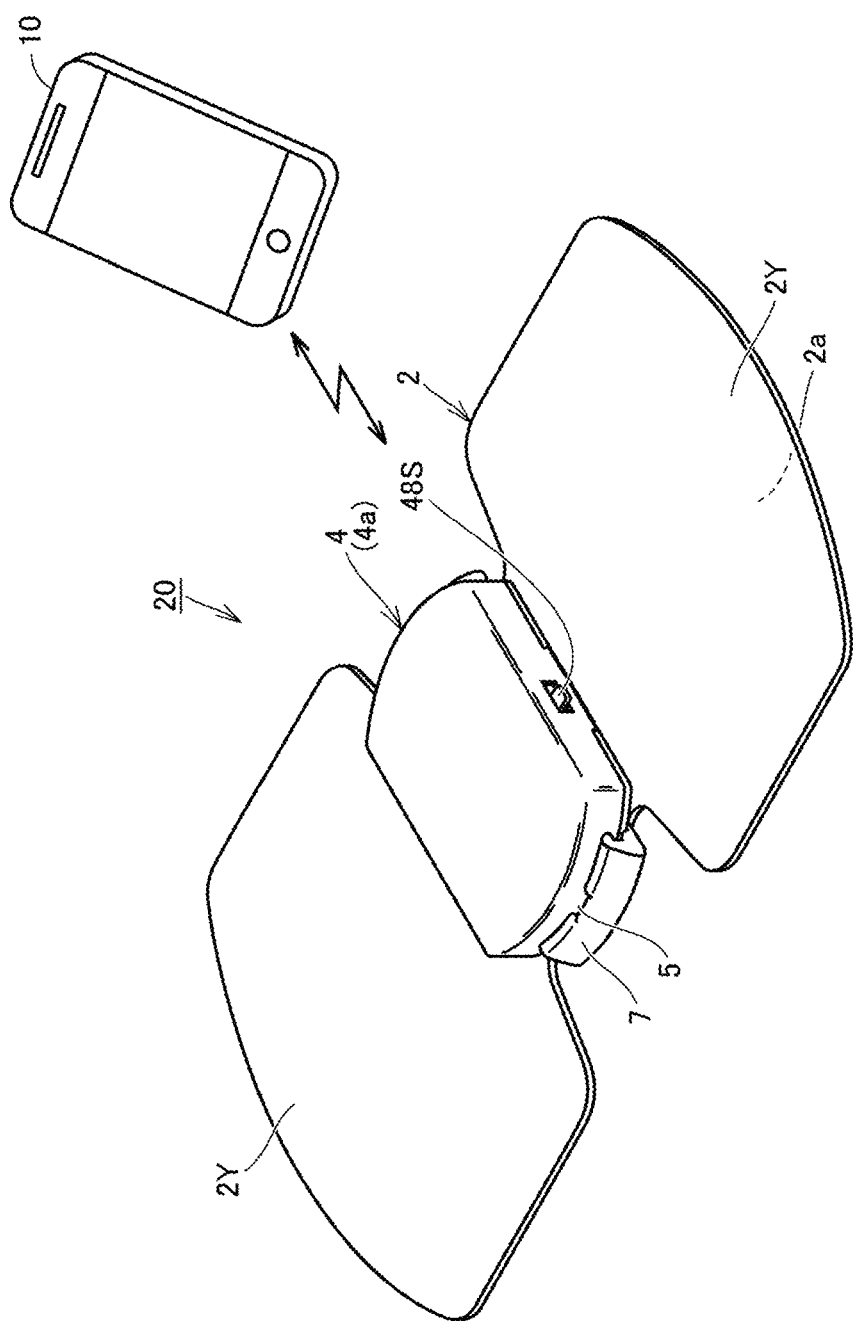
FIG. 20 is a diagram illustrating the appearance of a low-frequency treatment device 20.

FIG. 20 is a diagram illustrating the appearance of the low-frequency treatment device 20 according to the first embodiment in association with the terminal device 10. Referring to FIG. 20, the low-frequency treatment device 20 includes a pad 2, a holder 7, and a main body portion 4. The low-frequency treatment device 20 is a so-called cordless type and is controlled according to control information received from the terminal device 10.

The pad 2 is an example of a treatment portion that is configured to come into contact with an area of the body. The pad 2 has a sheet-like shape and is attached to an area of the user's body, specifically to the area to be treated or the like. A conductive layer 2a is provided on a surface (lower surface) of the outer surface of the pad 2 facing the body.

The pad 2 is attached to the user's skin using a conductive gel or the like, and a pulse current at a frequency corresponding to the treatment program is supplied to the user through the conductive layer 2a.

The pad 2 includes an attachment portion (not illustrated) and a treatment portion 2Y. The attachment portion is held by the holder 7. The holder 7 is positioned and disposed in the attachment portion. The treatment portion 2Y is provided on both the left and right sides of the attachment portion, and the conductive layer 2a is exposed on the surface of the treatment portion 2Y that faces the body. The conductive layer 2a is also exposed on the surface facing the body portion 4, and the exposed portion constitutes an electrode.

As illustrated in FIG. 20, the body portion 4 includes a case 4a with a substantially rectangular parallelepiped shape as an outer cover. An engagement portion 5 is formed between the case 4a and the holder 7, and the body portion 4 (case 4a) is detachably attached to the holder 7 by the engagement portion 5. The body portion 4 is provided with a switch 48S that is operated by a user to control the low-frequency treatment device 20. With the main body portion 4 attached to the holder 7, the main body portion 4 supplies a low-frequency pulse current to the conductive layer 2a of the pad 2. Specifically, the body portion 4 includes a built-in substrate, electric circuit mounted on the substrate, and the like.

In the treatment system 3, the terminal device 10 may include an acquisition unit that acquires the weather parameters of the position where the low-frequency treatment device 200 (or the terminal device 10) is located and a determination unit that determines whether the weather parameters are less than the thresholds. In this treatment system 3, at least one of the technological concepts described above may be used.

Also, the information described in FIG. 7, the information described in FIG. 13, and/or the information described in FIG. 17 may be notified of via the touch panel 158 of the terminal device 10. For example, in a case where the weather parameters are determined to be less than the thresholds, the touch panel 158 of the terminal device 10 may notify (of information illustrated in FIG. 13) saying to refrain from going outdoors in the time period when the weather parameters are less than the thresholds.

As described above, the low-frequency treatment device of the seventh embodiment may be a cordless type. Note that the acquisition unit, the adjustment unit, and the notification portion of the devices (low-frequency treatment device, terminal device) provided in the treatment system described referring to FIG. 1 and FIG. 19 may not be provided in these devices, and may be provided in another device or devices, as long as the embodiments described above can be achieved. For example, the acquisition unit may not be provided in the low-frequency treatment device, but may be provided in the terminal device.

Other Embodiments (1) The embodiments described above may include a first mode and a second mode selectable by the user. The first mode is a mode in which the intensity of the low frequency treatment is adjusted on the basis of the weather parameter and the threshold. That is, in the first mode, if the atmospheric pressure, i.e., weather parameter, is determined to be less than the first atmospheric pressure threshold, the intensity of the low frequency treatment is increased.

The second mode is a mode in which the intensity of the low frequency treatment is not adjusted regardless of the relationship between the weather parameter and the threshold (whether the weather parameter is greater or less than the threshold). That is, in the second mode, if the atmospheric pressure, i.e., weather parameter, is determined to be less than the first atmospheric pressure threshold, the intensity of the low frequency treatment is not changed (maintained at the same level).

Figure 21:
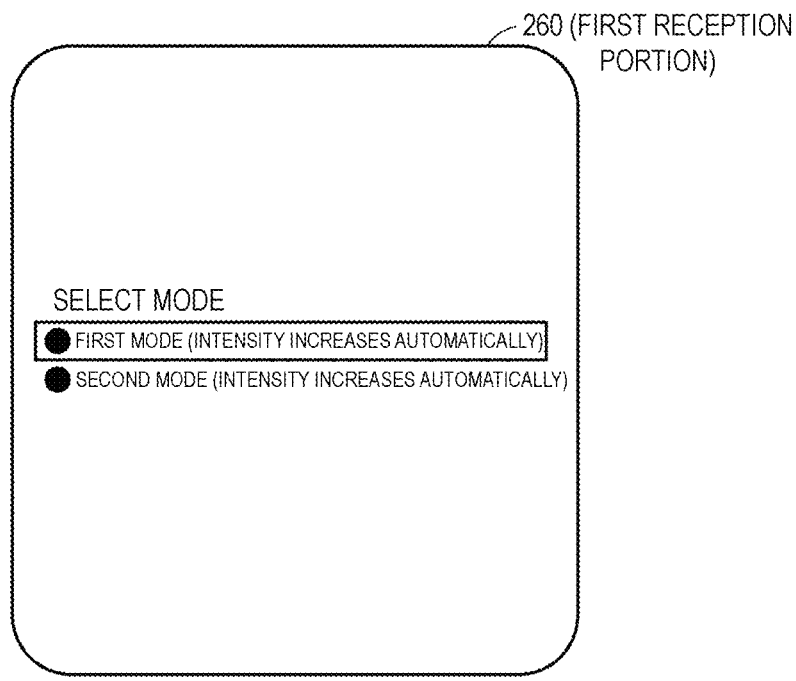
FIG. 21 is a diagram illustrating a first reception portion.

FIG. 21 is an example of a selection screen for receiving selection of the mode. The selection screen is displayed on the display 260. In the example of FIG. 21, the first mode and the second mode are displayed. The user can select one of the modes by moving the cursor to the mode. Note that in FIG. 21, a description of the first mode displayed, the description saying that if the weather parameter, i.e., atmospheric pressure, is determined to be less than the first atmospheric pressure threshold, the intensity of the low frequency treatment is increased. In FIG. 21, a description of the second mode is displayed, the description saying that if the atmospheric pressure, i.e., weather parameter, is determined to be less than the first atmospheric pressure threshold, the intensity of the low frequency treatment is not changed (maintained at the same level).

A user who desires the intensity of the low frequency treatment to automatically increase in the case where the weather parameter is determined to be less than the threshold can select the first mode. A user who does not desire the intensity of the low frequency treatment to automatically increase in the case where the weather parameter is determined to be less than the threshold can select the second mode.

In this way, the user can select the mode, thus further enhancing user convenience.

Note that as a modified example, the first mode may be a mode in which if the weather parameter, i.e., atmospheric pressure, is determined to be less than the first atmospheric pressure threshold, the intensity of the low frequency treatment is increased and, in a case where the atmospheric pressure is determined to be greater than the second atmospheric pressure threshold, the intensity of the low frequency treatment is decreased. The second mode may be a mode in which in a case where the weather parameter, i.e., atmospheric pressure, is determined to be less than the first atmospheric pressure threshold, the intensity of the low frequency treatment is not changed (maintained at the same level) and, in a case where the atmospheric pressure is determined to be greater than the second atmospheric pressure threshold, the intensity of the low frequency treatment is not changed (maintained at the same level).

The first mode may be a mode in which if the weather parameter, i.e., atmospheric pressure, is determined to be less than the first atmospheric pressure threshold, the intensity of the low frequency treatment is maintained at the same level and, if the atmospheric pressure is determined to be greater than the second atmospheric pressure threshold, the intensity of the low frequency treatment is decreased. In other words, the first mode may be a mode in which the intensity of the low frequency treatment is adjusted on the basis of the weather parameter and the threshold.

(2) In the embodiments described above, the atmospheric pressure threshold and the air temperature threshold are both preset values. However, in the treatment system described above, the atmospheric pressure threshold and/or the air temperature threshold can be set by the user. This setting can be received by, for example, the operation interface 230 or the touch panel 158 functioning as a second reception portion.

For example, a user who recognizes the atmospheric pressure at which body pain increases can set this atmospheric pressure as the atmospheric pressure threshold. Also, a user who recognizes the air temperature at which body pain increases can set this air temperature as the air temperature threshold.

Figure 22:
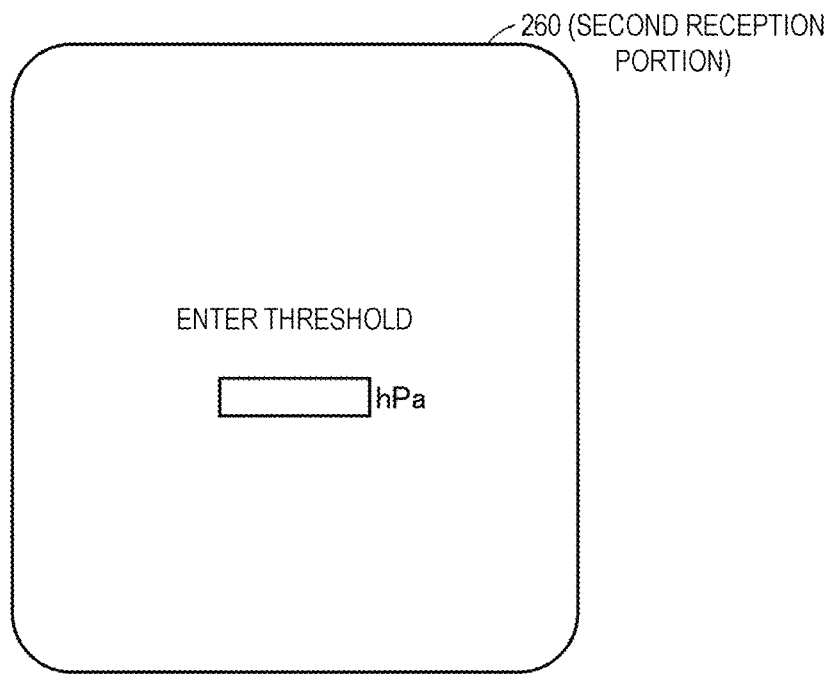
FIG. 22 is a diagram illustrating a second reception portion.

FIG. 22 is an example of an input screen for inputting a threshold. The input screen is displayed on the display 260. According to such a configuration, the user can set the atmospheric pressure threshold and/or the air temperature threshold. This allows the user to increase the intensity of the low frequency treatment and/or the intensity of the heat treatment at their convenience. Thus, the user convenience can be further enhanced.

Note that, as a modified example, the user may be able to set the first atmospheric pressure threshold, the second atmospheric pressure threshold, the first air temperature threshold, and/or the second air temperature threshold.

Figure 23:
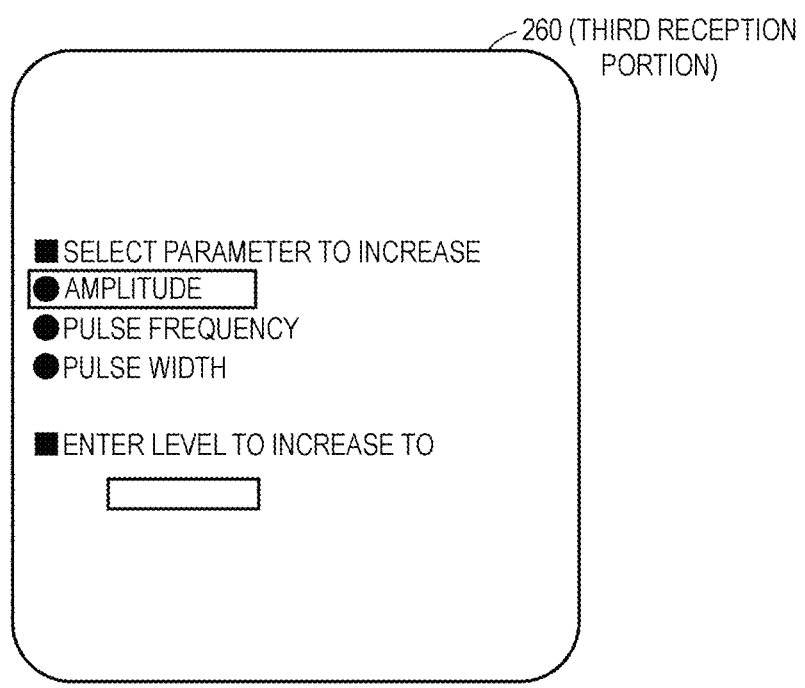
FIG. 23 is a diagram illustrating a third reception portion.

(3) In the treatment system described above, the user can set the target for "increasing intensity" to step S108 of FIG. 8, step S208 of FIG. 10, or both. FIG. 23 is an example of a selection screen for receiving selection of the target for "increasing intensity". The selection screen is displayed on the display 260. Also, in the example of FIG. 23, the user can input the increase level (value multiplied by the selected parameter (gain value)) for the selected parameter.

For example, when changing the treatment waveform, at least one of the three parameters described in relation to FIG. 5 (amplitude, pulse width, pulse frequency) can be selected as the parameter to be increased. For example, a user who does not want to feel uncomfortable when the intensity of the low frequency treatment is increased can select amplitude as the parameter to be increased. In another example, a user who wants to feel a difference when the intensity of the low frequency treatment is increased can select pulse width and/or pulse frequency as the parameter(s) to be increased. By allowing the user to select the parameter(s) to be increased in this way, user convenience is further enhanced. This setting can be received by, for example, the operation interface 230 or the touch panel 158 functioning as a third reception portion.

Furthermore, the value multiplied by the selected parameter (gain value) may be set by the user. For example, a user can set the gain value, and the low-frequency treatment device 200 can increase the intensity of the low frequency treatment and/or the heat treatment on the basis of the set gain value. This setting can be received by, for example, the operation interface 230 or the touch panel 158.

Such a configuration allows the user to set the intensity to their liking. This further increases user convenience.

Note that in a modified example, the user may be able to set "increase intensity target" and/or "increase level". In another modified example, the user may be able to set "decrease intensity target" and/or "decrease level". In other words, input of the intensity of the low frequency treatment adjustable by the adjustment unit may be receivable.

Modified Example (1) A specific member may be used as a treatment portion of the low-frequency treatment device. This specific member may be a member configured to emit heat (execute heat treatment), absorb heat (execute cooling treatment), and the like by the polarity of the current or the amount of current being changed. The specific member is typically a Peltier element. By using this specific member as the treatment portion to change the polarity of the current or the amount of current, heat treatment and cooling treatment can be selectively executed. Cooling treatment is generally considered to have an effect on acute pain (for example, a bruise).

With a low-frequency treatment device including such a specific member, an increase in temperature may result in the user's intended treatment (for example, cooling treatment) being unable to be performed due to the specific member also heating up. Thus, the low-frequency treatment device of the present modified example executes processing to cool the specific member. The processing to cool the specific member is, for example, processing to change the polarity of the current and/or processing to change the amount of current.

Also, with a low-frequency treatment device including the specific member, a decrease in temperature may result in the user's intended treatment (for example, heat treatment) being unable to be performed due to the specific member also cooling down. Thus, the low-frequency treatment device of the present modified example executes processing to heat the specific member. The processing to heat the specific member is, for example, processing to change the polarity of the current and/or processing to change the amount of current.

According to such a configuration, the low-frequency treatment device including the specific member can continue performing the user's intended treatment regardless of temperature changes that could render the low-frequency treatment device unable to perform the user's intended treatment.

(2) In the present embodiments described above, the low-frequency treatment device 200 can execute heat treatment in addition to low frequency treatment. However, another embodiment may relate to a heat treatment device configured to execute heat treatment and not low frequency treatment. For example, the concepts described in the second embodiment may be applied to the heat treatment device.

(3) In the first embodiment described above, in a case where the atmospheric pressure is determined to be less than the atmospheric pressure threshold, the intensity of the low-frequency treatment device is increased. However, in another embodiment, in a case where the air temperature is determined to be less than the air temperature threshold, the intensity of the low frequency treatment is increased. In the second embodiment described above, in a case where the air temperature is determined to be less than the air temperature threshold, the intensity of the heat treatment device is increased. However, in another embodiment, in a case where the atmospheric pressure is determined to be less than the atmospheric pressure threshold, the intensity of the heat treatment is increased.

Also, in the embodiments described above, atmospheric pressure and air temperature are used as weather parameters that causes an increase of body pain of the user. However, other parameters may be used.

(4) In the embodiments described above, the low-frequency treatment device 200 or the terminal device 10 acquires the weather parameter from the weather server. However, the low-frequency treatment device 200 or the terminal device 10 may include a parameter detection unit (sensor), and the parameter detection unit may detect the weather parameter and the acquisition unit may acquire the detected weather parameter. With such a configuration, the treatment system does not need to be provided with the weather server 30.

(5) In the embodiments described above, the notifications of FIG. 7, FIG. 13, FIG. 17, and the like are displayed on the display 260. However, the notifications may be voice notifications. The notifications may also be a combination of a display on the display 260 or the like and a voice notification.

Figure 24A:
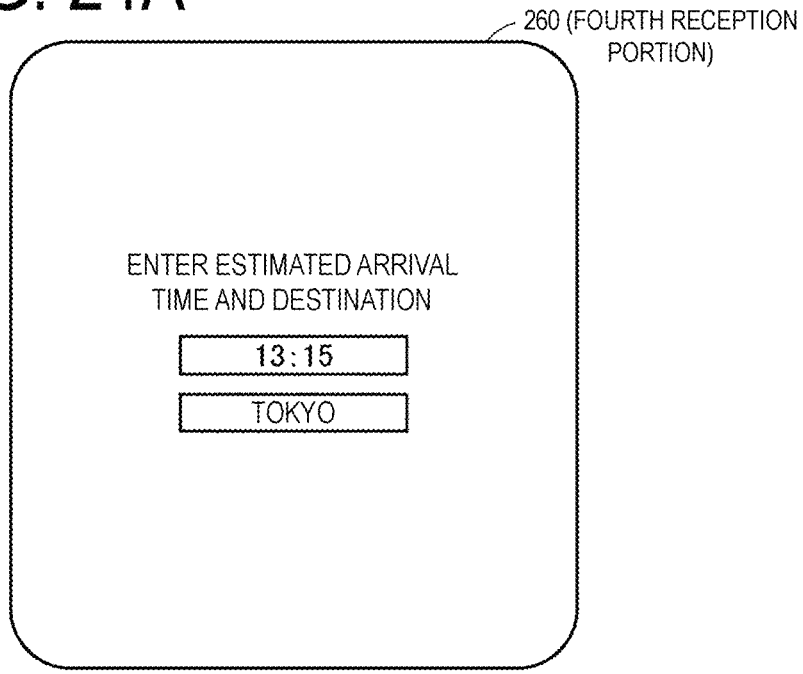
FIGS. 24A and 24B are diagrams illustrating a fourth notification portion.
Figure 24B:
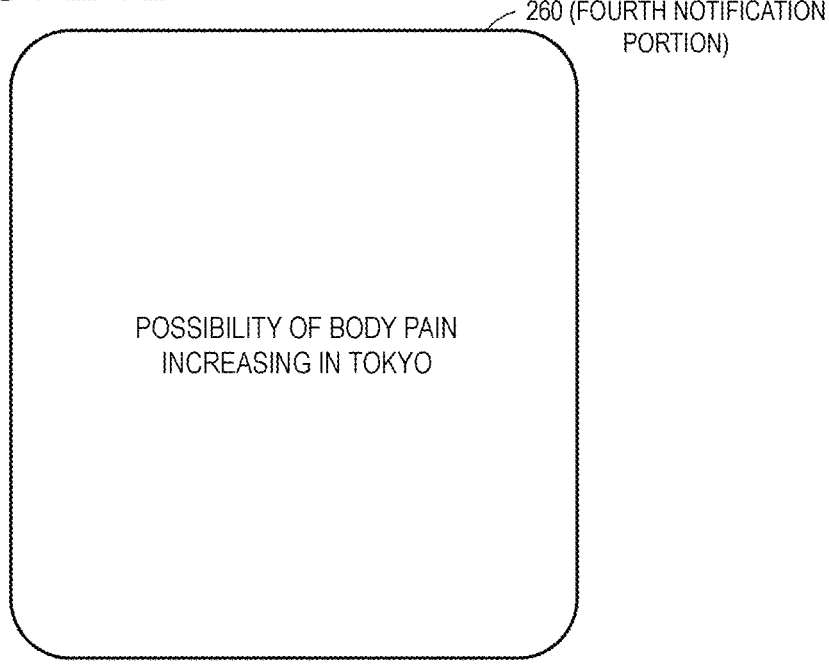

(6) The user may be able to input a travel destination (position) to the low-frequency treatment device or the terminal device and may be notified of the possibility of body pain increasing when at the destination. FIGS. 24A and 24B are diagrams for describing the present modified example. An example of the system configuration of the present modified example is illustrated in FIG. 1.

In the example of FIG. 24A, the characters "enter your estimated arrival time and destination" are displayed on the display 260. Additionally, in the example of FIG. 24A, the user can input a destination (position (place)) of the destination of the user) and an estimated arrival time at the destination to the display 260 functioning as a fourth reception portion. In the example of FIG. 24A, "13:15" has been entered as the estimated arrival time and "Tokyo" has been entered as the "destination (travel position (place)).

In the case where an input such as that illustrated in FIG. 24A is executed, a display screen such as that illustrated in FIG. 24B is displayed on the display 260 functioning as the fourth notification portion. In the example of FIG. 24B, the characters "possibility of body pain increasing in Tokyo" are displayed. In this way, the low-frequency treatment device of the present modified example notifies the user of the possibility of body pain increasing at the input position and time.

Figure 25:
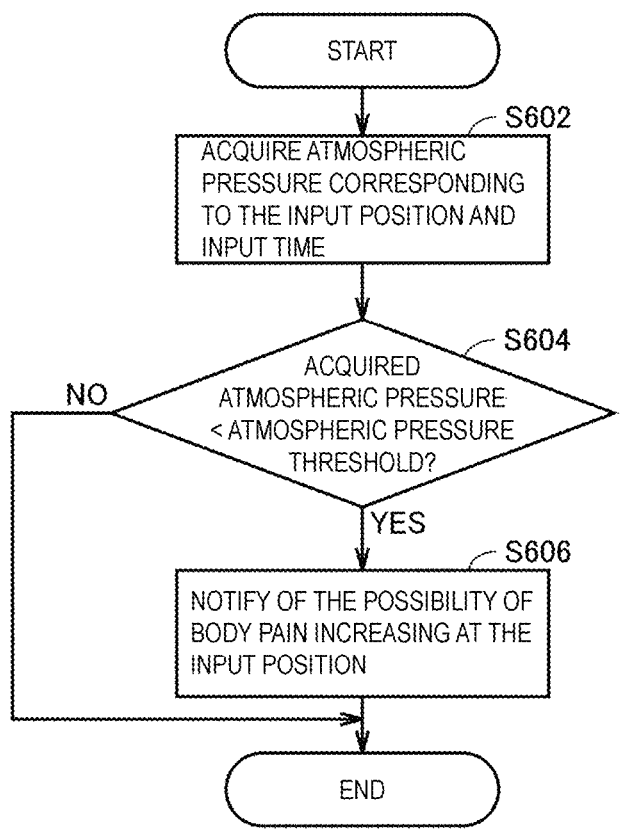
FIG. 25 is a diagram illustrating a flowchart relating to a low-frequency treatment device.

FIG. 25 is a diagram illustrating a flowchart relating to a low-frequency treatment device of a modified example. The low-frequency treatment device sends to a weather server position information indicating an input position (for example, longitude and latitude) and time information indicating an input time. In the example of FIGS. 24A and 24B, the position information is position information indicating Tokyo and the time information is time information indicating 13:15. The weather server sends to the low-frequency treatment device the atmospheric pressure corresponding to the position information and the time information received from the low-frequency treatment device. The weather server stores a table including position information and time information and atmospheric pressure associated together. The weather server references the table and extracts the atmospheric pressure corresponding to the position information and the time information received from the low-frequency treatment device and sends the extracted atmospheric pressure to the low-frequency treatment device.

In step S602, the low-frequency treatment device acquires the atmospheric pressure corresponding to the received atmospheric pressure, i.e., the atmospheric pressure corresponding to the input position and input time. Next, in step S604, the low-frequency treatment device determines whether the acquired atmospheric pressure is less than the atmospheric pressure threshold (corresponding to the first atmospheric pressure threshold described above). If YES is determined in step S604, in step S606, a display such as "possibility of body pain increasing present at input position" is displayed. The display is, for example, the display illustrated in FIG. 24B.

A low-frequency treatment device of the present modified example notifies the user of the possibility of body pain increasing at the input position and time. Thus, the user can be made aware of where there is a possibility of body pain increasing at the user's destination.

(7) In the example of FIG. 6, the function of the determination unit and the function of the adjustment unit are listed separately. However, for example, the function of the adjustment unit may be included together with the function of the determination unit.

(8) In the example of FIG. 8 and FIG. 18, if YES is determined in step S104, i.e., if the atmospheric pressure is determined to be less than the first atmospheric pressure threshold, the intensity of the low frequency treatment is increased. In a state where the low frequency treatment has an increased intensity, if the atmospheric pressure is determined to be greater than the first atmospheric pressure threshold, the intensity of the low frequency treatment may be decreased (for example, the intensity may be reduced to the pre-increased intensity). In this way, in the case where the atmospheric pressure is determined to be less than the first atmospheric pressure threshold, typically the body pain of the user increases, and in the case where the atmospheric pressure is greater than the first atmospheric pressure threshold, typically the body pain of the user decreases. Thus, by decreasing the intensity of the low frequency treatment, no discomfort is caused to the user and power consumption of the low-frequency treatment device can be reduced.

The embodiments described herein are illustrative in all respects and are not intended as limitations. The scope of the present invention is indicated not by the descriptions above but by the claims and includes all meaning equivalent to the scope and changes within the scope.

REFERENCE SIGNS LIST

10 Terminal device
30 Weather server
40 Facility server
200 Low-frequency treatment device
302 Acquisition unit
304 Determination unit

The invention claimed is:

1. A low-frequency treatment device, comprising:
   one or more processors configured to acquire an atmospheric pressure or an air temperature for a position where the low-frequency treatment device is located;
   a treatment portion, including a pad, configured to perform low frequency treatment;
   in a case where the atmospheric pressure or the air temperature that is acquired is determined to be less than a first threshold, the one or more processors are further configured to adjust and increase an intensity of the low frequency treatment, and
   in a case where the atmospheric pressure or the air temperature that is acquired is determined to be less than the first threshold, notify, via a display, an action to be taken by the user when the atmospheric pressure or the air temperature is less than the first threshold.

2. The low-frequency treatment device according to claim 1, wherein the one or more processors are further configured to
   generate a treatment current and to execute processing to increase the intensity of the low frequency treatment by increasing an amplitude of a waveform of the treatment current.

3. The low-frequency treatment device according to claim 1, wherein
   the treatment portion is configured to perform heat treatment; and
   one or more processors are further configured to, when the atmospheric pressure or the air temperature that is acquired is determined to be less than the first threshold, adjust and increase an intensity of the heat treatment.

4. The low-frequency treatment device according to claim 1, further comprising
   the display configured to, in a case where the atmospheric pressure or the air temperature that is acquired is determined to be less than the first threshold, notify saying to refrain from going outdoors in a time period when the atmospheric pressure or the air temperature is less than the first threshold.

5. The low-frequency treatment device according to claim 1,
   wherein the one or more processors are further configured to receive input of position information, and acquire an atmospheric pressure or an air temperature for a position indicated by the position information that is received via input; and
   wherein the low-frequency treatment device further includes the display configured to, when the atmospheric pressure or the air temperature for a position indicated by the position information that is acquired is determined to be less than the first threshold, notify of a possibility of body pain of a user increasing.

6. The low-frequency treatment device according to claim 1, wherein
   a second threshold is greater than a first threshold; and
   the one or more processors are further configured to, when the atmospheric pressure or the air temperature that is acquired is determined to be greater than the second threshold, adjust and decrease the intensity of the low frequency treatment.

7. The low-frequency treatment device according to claim 1, further comprising
   a user interface configured to receive from a user a mode that is set, the mode comprising a first mode in which the intensity of the low frequency treatment is adjusted, and a second mode in which the intensity of the low frequency treatment is not adjusted.

8. A low-frequency treatment device, comprising:
   one or more processors configured to acquire an atmospheric pressure or an air temperature for a position where the low-frequency treatment device is located;
   a treatment portion, including a pad, configured to perform low frequency treatment;
   in a case where the atmospheric pressure or the air temperature that is acquired is determined to be greater than a second threshold, the one or more processors are further configured to adjust and decrease an intensity of the low frequency treatment, and
   in a case where the atmospheric pressure or the air temperature that is acquired is determined to be greater than the second threshold, notify, via a display, an action to be taken by the user when the atmospheric pressure or the air temperature is greater than the second threshold.

9. The low-frequency treatment device according to claim 8, wherein
   the treatment portion is configured to perform heat treatment; and
   the one or more processors are further configured to, in a case where the atmospheric pressure or the air temperature that is acquired is determined to be greater than the second threshold, adjust and decrease an intensity of the heat treatment.

10. A treatment system, comprising:
a low-frequency treatment device including a pad that performs low frequency treatment;
a terminal device configured to communicate with the low-frequency treatment device
and includes one or more processors configured to acquire an atmospheric pressure or an air temperature for a position where the low-frequency treatment device is located; wherein
the terminal device is configured to, in a case where the atmospheric pressure or the air temperature that is acquired is determined to be less than a threshold, notify, via a display, saying to refrain from going outdoors in a time period when the atmospheric pressure or the air temperature is less than the threshold.

* * * * *